US007820972B2

(12) United States Patent
Miyamae et al.

(10) Patent No.: US 7,820,972 B2
(45) Date of Patent: Oct. 26, 2010

(54) METHOD OF EVALUATING SKIN CONDITIONS AND METHOD OF ESTIMATING SKIN THICKNESS

(75) Inventors: Yuta Miyamae, Yokohama (JP); Yumika Yamakawa, Yokohama (JP); Junko Tsuchiya, Yokohama (JP); Marie Kawabata, Yokohama (JP)

(73) Assignee: Pola Chemical Industries Inc., Shizuoka-shi, Shizuoka (JP)

( * ) Notice: Subject to any disclaimer, the term of this patent is extended or adjusted under 35 U.S.C. 154(b) by 211 days.

(21) Appl. No.: 12/064,001

(22) PCT Filed: Sep. 1, 2006

(86) PCT No.: PCT/JP2006/317360
§ 371 (c)(1),
(2), (4) Date: Feb. 15, 2008

(87) PCT Pub. No.: WO2007/026884
PCT Pub. Date: Mar. 8, 2007

(65) Prior Publication Data
US 2009/0134331 A1 May 28, 2009

(30) Foreign Application Priority Data
Sep. 2, 2005 (JP) .............................. 2005-254324
Sep. 2, 2005 (JP) .............................. 2005-254326
Sep. 27, 2005 (JP) .............................. 2005-279292

(51) Int. Cl.
*A61B 5/00* (2006.01)
(52) U.S. Cl. .............................. 250/339.11; 250/341.8; 600/306; 600/310; 600/473
(58) Field of Classification Search .............. 250/338.1, 250/339.01, 339.06, 339.11, 339.12, 340, 250/341.1, 341.2, 341.8; 600/306, 310, 473; 607/100
See application file for complete search history.

(56) References Cited

U.S. PATENT DOCUMENTS

| | | | |
|---|---|---|---|
| 6,501,982 B1 * | 12/2002 | Ruchti et al. | 600/473 |
| 6,675,029 B2 * | 1/2004 | Monfre et al. | 600/310 |
| 2001/0041829 A1 | 11/2001 | Thennadil et al. | |

(Continued)

FOREIGN PATENT DOCUMENTS

JP    11-290315    10/1999

(Continued)

OTHER PUBLICATIONS

International Search Report dated Sep. 26, 2006.

(Continued)

*Primary Examiner*—David P Porta
*Assistant Examiner*—David S Baker
(74) *Attorney, Agent, or Firm*—Knobbe, Martens, Olson & Bear, LLP

(57) ABSTRACT

Methods of determining at least one of the degree of skin damage caused by UV light and the degree of physiologically aging of the skin, and methods of estimating at least one of an epidermal skin thickness and a dermal skin thickness by analysis of the near infrared absorption spectrum of skin are disclosed. The near infrared absorption spectrum of skin are analyzed and the obtained analysis result is used for monitoring skin conditions and evaluating cosmetics.

11 Claims, 28 Drawing Sheets

U.S. PATENT DOCUMENTS

| | | | |
|---|---|---|---|
| 2003/0060693 A1* | 3/2003 | Monfre et al. | 600/322 |
| 2003/0208111 A1 | 11/2003 | Mattu et al. | |
| 2004/0125996 A1* | 7/2004 | Eddowes et al. | 382/128 |
| 2004/0142402 A1 | 7/2004 | Maruo et al. | |
| 2004/0236229 A1* | 11/2004 | Freeman et al. | 600/474 |
| 2008/0161661 A1* | 7/2008 | Gizewski | 600/306 |
| 2008/0194928 A1* | 8/2008 | Bandic et al. | 600/306 |

FOREIGN PATENT DOCUMENTS

| | | |
|---|---|---|
| JP | 11-299792 | 11/1999 |
| JP | 2000-083954 | 3/2000 |
| JP | 2001-161364 | 6/2001 |
| JP | 2001-212087 | 8/2001 |
| JP | 2002-090298 | 3/2002 |
| JP | 2002-330943 | 11/2002 |
| JP | 2002-360544 | 12/2002 |
| JP | 2003-270138 | 9/2003 |
| JP | 2003-344279 | 12/2003 |
| JP | 2004-354159 | 12/2004 |
| JP | 2005-034350 | 2/2005 |
| JP | 2005-083901 | 3/2005 |
| JP | 2005-095326 | 4/2005 |
| WO | WO 01/53805 | 7/2001 |
| WO | WO 01/75421 | 10/2001 |
| WO | WO 03/041582 | 5/2003 |

OTHER PUBLICATIONS

Yakujinippo, Ltd., Supervised by Katsuyuki Takeda, Shotaro Harada and Masanori Ando; edited by the Society of Cosmetic Chemists of Japan (SCCJ), "Functional Cosmetology-Substantiation of Cosmetics Efficacy: Recent Progress and Future Promise," pp. 51-53, 2001.

Yakujinippo, Ltd., Supervised by Katsuyuki Takeda, Shotaro Harada and Masanori Ando; edited by the Society of Cosmetic Chemists of Japan (SCCJ), "Functional Cosmetology-Substantiation of Cosmetics Efficacy: Recent Progress and Future Promise," pp. 163-177, 2001.

Supplementary Partial European Search Report dated Feb. 4, 2010 and issued to corresponding European patent application No. EP 06 79 7302.4.

* cited by examiner

METHOD OF EVALUATING SKIN CONDITIONS AND METHOD OF ESTIMATING SKIN THICKNESS

CROSS-REFERENCE TO RELATED APPLICATIONS

This application is the U.S. National Phase under 35 U.S.C. §371 of International Application PCT/JP2006/317360, filed Sep. 1, 2006, which was published in a non-English language, which claims priority to JP Application No. 2005-254324, filed Sep. 2, 2005, JP Application No. 2005-254326, filed Sep. 2, 2005, and JP Application No. 2005-279292, filed Sep. 27, 2005.

TECHNICAL FIELD

The present invention relates to a method of determining at least one of a degree of skin damage caused by UV light and a degree of physiological aging of the skin, a method of estimating at least one of the epidermal thickness and dermal thickness of the skin, and a method of monitoring the skin conditions, a method of evaluating cosmetics, and the like, by using results obtained in the above methods.

BACKGROUND ART

Everyone as well as women desire to have a beautiful skin. Therefore, under present circumstances, most women try to keep the skin in preferable conditions, using cosmetics and the like. The skin conditions vary largely depending upon the individuals. The skin aging is roughly classified into physiological aging (original physiological aging) that occur in every human being along with aging, and pathological aging caused by UV light (damage caused by UV light, or photo-aging) (for example, see Non-patent Document 1).

Due to the skin aging, changes with time, such as the loss of elasticity and the increase in wrinkles occur, which have a great influence on the appearance and impression. Such changes with time reflect the physiological changes among the skin, in particular, in the epidermis and dermis constituting the skin, and for example, shallow wrinkles are greatly influenced by the epidermis and papillary layer, whereas deep wrinkles and sagging are greatly influenced by the dermis (for example, see Non-patent Document 2). Thus, in order to keep the skin beautifully, it is very important to judge the conditions such as each thickness of the epidermis and dermis objectively and quantitatively, which makes it possible to select and use appropriate cosmetics and medicine suitable for the skin conditions, or conduct doctor's treatment and the like.

As such a method of measuring physiological or aging changes of a skin, a method of estimating an actual age by measuring an external appearance of wrinkles or sagging (for example, see Patent Documents 1 and 2), a method of estimating a skin age based on the measurement results of a skin surface form (for example, see Patent Document 3), a method of calculating a skin age based on changes in vibration obtained when a skin is brought into contact with a vibrator (for example, see Patent Document 4), a method of estimating an age based on the dermal brightness from an ultrasonic skin image (for example, see Patent Document 5), a method of evaluating the stiffening effect of a skin based on the thickness of the skin from an ultrasonic image (for example, see Patent Document 6), and the like are disclosed. Further, a method of estimating an age using an average area of a horny layer cell of a epidermis as an index (for example, see Patent Document 7), a method of evaluating the degree of skin aging by measuring changes in a force generated by a fibroblast (for example, see Patent Document 8), a method of evaluating the degree of skin aging using a DNA (for example, see Patent Document 9), and the like are disclosed. However, none of the above discloses a method of determining damage caused by UV light and physiological aging, and a method of estimating each thickness of an epidermis and a dermis objectively and quantitatively.

In recent years, a procedure of measuring a near infrared absorption spectrum of a tissue, a skin, and a hair of a human being, performing a statistical treatment (multivariate analysis) such as multiple regression analysis and principal component analysis with respect to spectrometry and specific values such as moisture and a tissue state, and based on a correlation thereof, clarifying a skin moisture, mammitis, hair conditions, and the like noninvasively has been known (for example, see Patent Documents 10-13). Further, quantification of the existing amount of dermal collagen of a skin (for example, see Patent Document 14). However, none of those discloses a method of determining skin damage caused by UV light and physiological aging, and a method of estimating each thickness of an epidermis and a dermis objectively and quantitatively.

Under such circumstances, the inventors of the present invention have found, in judging the skin conditions such as a skin thickness, a skin surface form, a skin viscoelasticity, or skin internal tissue structure, that the thickness of a skin can be judged noninvasively by using multivariate analysis of a near infrared absorption spectrum, and filed a patent application (Patent Document 15). In order to select and use appropriate cosmetics and medicine suitable for skin conditions, there is a demand for developing means for further advancing this technology, and measuring each thickness of an epidermis and a dermis constituting a skin noninvasively and objectively.

Patent Document 1: JP 2002-330943 A
Patent Document 2: JP 2002-360544 A
Patent Document 3: JP 2005-095326 A
Patent Document 4: JP 2001-212087 A
Patent Document 5: JP 2000-083954 A
Patent Document 6: JP 11-290315 A
Patent Document 7: JP 11-299792 A
Patent Document 8: JP 2004-354159 A
Patent Document 9: JP 2001-161364 A
Patent Document 10: JP 2002-090298 A
Patent Document 11: JP 2003-344279 A
Patent Document 12: WO 01-075421 A
Patent Document 13: JP 2003-270138 A
Patent Document 14: JP 2005-083901 A
Patent Document 15: JP 2005-034350 A
Non-patent Document 1: "Utility of Cosmetics" edited by THE SOCIETY OF COSMETIC CHEMISTS OF JAPAN, Yakuji Nippo Ltd., 51-52, 2001
Non-patent Document 2: "Utility of Cosmetics" edited by THE SOCIETY OF COSMETIC CHEMISTS OF JAPAN, Yakuji Nippo Ltd., 163, 178, 2001

DISCLOSURE OF THE INVENTION

Problems to be Solved by the Invention

The present invention has been made under such circumstances, and an object thereof is to provide a method of determining at least one of the degree of skin damage caused by UV light and the degree of physiological aging of the skin, a method of estimating at least one of an epidermal skin thickness and a dermal skin thickness, and a method of monitoring skin conditions and a method of evaluating cosmetics, using the results of the above methods.

Means for Solving the Problems

The inventors of the present invention have earnestly studied in view of the above situations. Consequently, first, the inventors of the present invention obtained a correlation between the characteristic values of skins and the near infrared absorption spectrum thereof based on the analysis results of multivariate analysis of the near infrared absorption spectrum of two or more kinds of skins whose characteristic values (the degree of skin damage caused by UV light, the degree of skin physiological aging, the epidermal thickness, and the dermal thickness) are known, then, obtained the near infrared absorption spectrum of a skin whose characteristic values are unknown, which is to be determined or estimated, found that the above characteristic value can be determined or estimated from the near infrared absorption spectrum of the skin whose characteristic values are unknown, based on the above correlation, and thus, achieved the present invention. More specifically, the present invention relates to the following technologies.

(1) A method of determining at least one of a degree of damage of a skin caused by UV light and a degree of physiological aging of the skin from a near infrared absorption spectrum of the skin, including the steps of:

(X1) obtaining a correlation between at least one of the degree of damage of the skin caused by UV light and the degree of physiological aging of the skin and a near infrared absorption spectrum of the skin in a particular wave number region, from analysis results of multivariate analysis of the near infrared absorption spectrum in the particular wave number region in a measurement wave number region of 5990 to 5490 cm$^{-1}$ and 5000 to 4480 cm$^{-1}$ of two or more kinds of skins in which at least one of the degree of damage of the skin caused by UV light and the degree of physiological aging of the skin is known;

(X2) obtaining a near infrared absorption spectrum in a particular wave number region of a skin in which at least one of the degree of damage of the skin caused by UV light and the degree of physiological aging of the skin to be evaluated is unknown; and (X3) determining at least one of the degree of damage of the skin caused by UV light and the degree of physiological aging of the skin from the near infrared absorption spectrum in the particular wave number region obtained in the Step (X2) based on the correlation obtained in the Step (X1).

(2) A method according to Item (1), in which both the degree of damage of the skin caused by UV light and the degree of physiological aging of the skin are determined simultaneously.

(3) A method according to Item (1) or (2), in which the multivariate analysis is a principal component analysis (PCA) method, SIMCA method or a KNN method.

(4) A method of estimating at least one of an epidermal thickness and a dermal thickness of a skin from a near infrared absorption spectrum of the skin, including the steps of:

(Y1) obtaining a correlation between at least one of an epidermal thickness and a dermal thickness of a skin and a near infrared absorption spectrum in a particular wave number region of the skin, from analysis results of multivariate analysis of the near infrared absorption spectrum in the particular wave number region in measurement wave number regions of 6850 to 6620 cm$^{-1}$, 6540 to 5990 cm$^{-1}$, 5240 to 5180 cm$^{-1}$, 5030 to 4980 cm$^{-1}$, 4760 to 4720 cm$^{-1}$, and 4650 to 4610 cm$^{-1}$, or 6940 to 6850 cm$^{-1}$, 6710 to 6540 m$^{-1}$, 6250 to 6170 cm$^{-1}$, 5130 to 5080 cm$^{-1}$, 4950 to 4850 cm$^{-1}$, 4760 to 4690 cm$^{-1}$, and 4670 to 4610 cm$^{-1}$ of two or more kinds of skins in which at least one of an epidermal thickness and a dermal thickness of a skin is known;

(Y2) obtaining a near infrared absorption spectrum in a particular wave number region of a skin in which at least one of an epidermal thickness and a dermal thickness of the skin to be estimated is unknown; and (Y3) estimating at least one of the epidermal thickness and the dermal thickness of the skin from the near infrared absorption spectrum in the particular wave number region obtained in the Step (Y2) based on the correlation obtained in the Step (Y1).

(5) A method according to Item (3), in which both the epidermal thickness and the dermal thickness of the skin are estimated simultaneously.

(6) A method according to Item (4) or (5), in which the multivariate analysis is a partial least squares (PLS) method or a principal component regression (PCR) analysis method.

(7) A method of selecting a cosmetic, including the step of selecting a cosmetic using the method according to any one of Items (1) to (6).

(8) A method of monitoring a skin condition, including the step of capturing a change of the skin with time chronologically using the method according to any one of Items (1) to (6).

(9) A method of monitoring according to Item (8), including the step of confirming effects of treatment with respect to the skin.

(10) A method of evaluating a cosmetic, including the step of comparing a state or a thickness of the skin before and after administration of the cosmetic and evaluating the cosmetic with the change as an index, using the method according to any one of Items (1) to (6).

(11) A method of evaluating a cosmetic according to Item (10), including the step of evaluating that a cosmetic has a wrinkle eliminating function in a case where a thickness of a dermis in the thickness of the skin increases due to the administration of the cosmetic.

EFFECTS OF THE INVENTION

According to the present invention, a method of evaluating at least one of the degree of skin damage caused by UV light and the degree of physiological aging of a skin noninvasively, a method of estimating at least one of the epidermal thickness and dermal thickness noninvasively, and a method of monitoring skin conditions and a method of evaluating cosmetics, using the results of those methods can be provided.

BEST MODE FOR CARRYING OUT THE INVENTION

Figure 1:
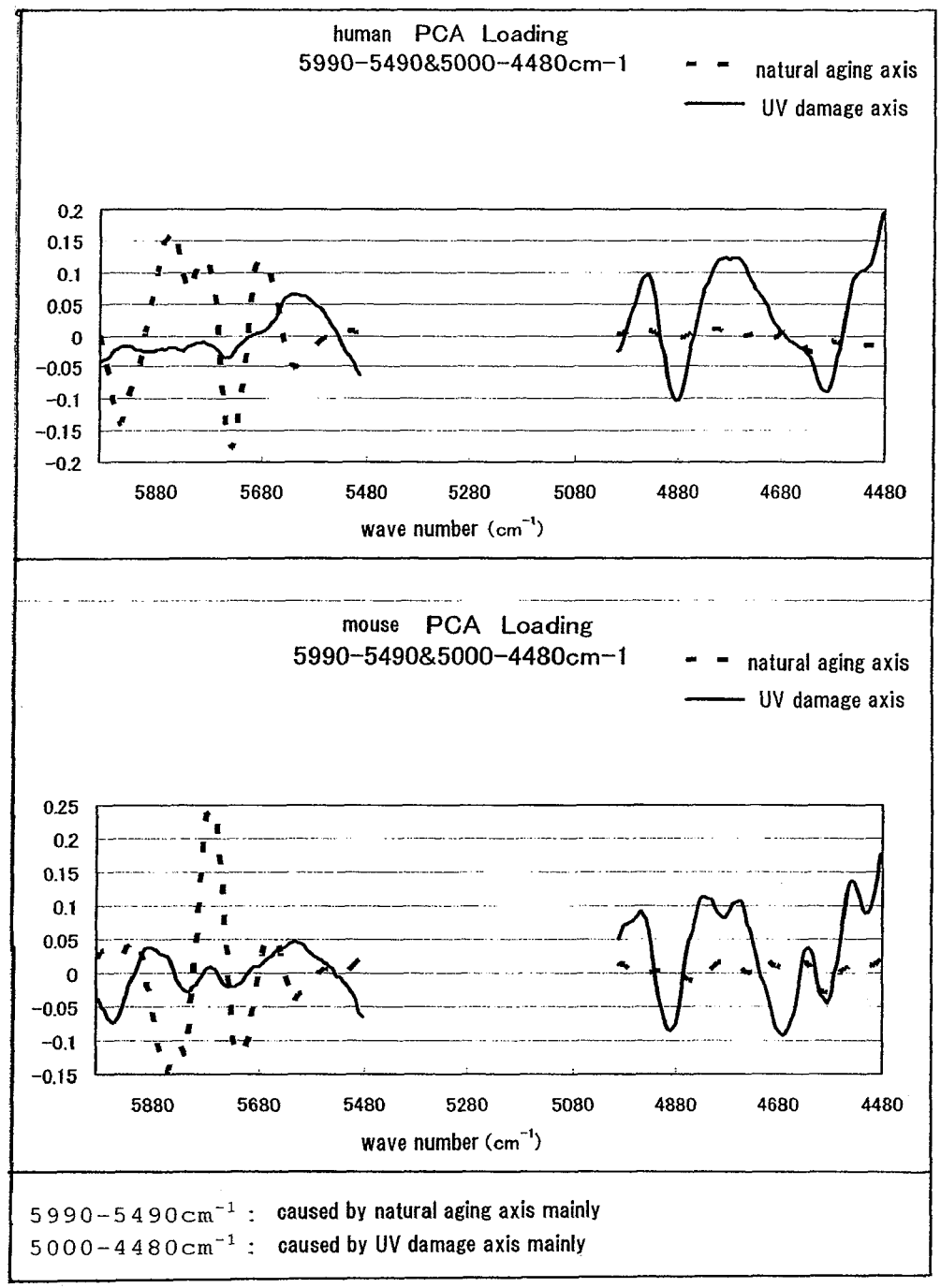
FIG. 1 is a diagram showing loading (factor load amount) characteristics of near infrared absorption spectra of a hairless mouse and a human being.

The method of the present invention has a feature in that: (1) the correlation between the characteristic values of skins and the near infrared absorption spectra thereof is obtained from the analysis results of multivariate analysis of the near infrared absorption spectra of two or more kinds of skins whose characteristic values are known; (2) a near infrared absorption spectrum of a skin whose characteristic values are unknown, which is to be determined or estimated, is obtained; and (3) the characteristic value is determined or estimated from the near infrared absorption spectrum of the skin whose characteristic values are unknown, based on the above correlation.

The above characteristic value of a skin refers to the degree of skin damage caused by UV light, the degree of physiological aging of a skin, the thickness of an epidermis of a skin, or the thickness of a dermis of a skin.

The skin damage caused by UV light is classified into an acute reaction such as a sunburn, and a chronic reaction in which skin aging (which is also referred to as photoaging) such as spots and wrinkles caused by long-term exposure to UV light, skin cancer, and the like. The "skin damage caused by UV light" in the present application means the influence of relatively long-term exposure to UV light, and the near infrared absorption spectrum of a skin injured by UV light changes in a wave number region of 5000 to 4480 $cm^{-1}$. The change in the wave number region is assumed to be caused by the structural change of a protein (see FIG. 1). Further, the "physiological aging" in the present application means the influence of natural aging such as shrinkage and wrinkles of a skin that is not exposed to UV light, and the near infrared absorption spectrum of a skin having physiological aging changes in a wave number region of 5990 to 5490 $cm^{-1}$. The change in the wave number region is assumed to be caused by changes in collagen, elastin, skinthickness, ceramide, and the like (see FIG. 1).

The "degree of damage caused by UV light" means the irradiation amount of UV light to a skin or a site difference. The site difference means that an exposure sites such as a front arm outer side portion and a face surface are likely to be exposed to UV light, whereas a non-exposure sites such as an upper limb inner side portion and a trunk portion is unlikely to be exposed to UV light.

Further, the "degree of physiological aging" means the degree of natural aging in which exposure to UV light does not occur, and means an age in week (a mouse, etc.) or an actual age.

The skin is an organ that covers the surface of a body and functions as a boundary with an outside, and is composed to three layers of an epidermis, a dermis, and a hypodermis. Changes that have great weight in terms of beauty, such as wrinkles, sagging, and elasticity of a skin reflect the physiological changes of an epidermis or a dermis constituting the skin. Thus, it is very useful to know each thickness of an epidermis and a dermis constituting a skin in terms of beauty and the use of cosmetics. The "thickness of a skin" as used herein means the thickness of an epidermis and a dermis.

The method according to the present invention can be used for determining at least one of the degree of skin damage caused by UV light and the degree of physiological aging of a skin, or for estimating at least one of an epidermal thickness and a dermal thickness of a skin. The skin as used herein refers to a skin of animals such as a human being and a mouse.

A method of determining of the present invention includes the steps of:

(X1) obtaining a correlation between at least one of the degree of damage of the skin caused by UV light and the degree of physiological aging of the skin and a near infrared absorption spectrum of the skin in a particular wave number region, from analysis results of multivariate analysis of the near infrared absorption spectrum in the particular wave number region in a measurement wave number region of 5990 to 5490 cm$^{-1}$ and 5000 to 4480 cm$^{-1}$ of two or more kinds of skins in which at least one of the degree of damage of the skin caused by UV light and the degree of physiological aging of the skin is known;

(X2) obtaining a near infrared absorption spectrum in a particular wave number region of a skin in which at least one of the degree of damage of the skin caused by UV light and the degree of physiological aging of the skin to be evaluated is unknown; and (X3) determining at least one of the degree of damage of the skin caused by UV light and the degree of physiological aging of the skin from the near infrared absorption spectrum in the particular wave number region obtained in the Step (X2) based on the correlation obtained in the Step (X1).

The near infrared absorption spectrum of a skin in the Step (X1) can be obtained by an arbitrary method. For example, the near infrared absorption spectrum can be obtained by measurement, using various types of near infrared absorption spectrum measurement apparatuses. More specifically, the near infrared absorption spectrum is measured with a dispersion-type measurement apparatus using a diffraction grating, or a measurement apparatus using a diode array as a detector. Further, the measured near infrared absorption spectrum of a skin may be subjected to a Fourier transform.

The multivariate analysis in the Step (X1) means the pattern recognition for clarifying the relationship between samples (the degree of skin damage caused by UV light and the degree of physiological aging of a skin in the present invention) by calculating a similarity or the like based on a plurality of observation values (herein, near infrared absorption spectrum data). The multivariate analysis method in the Step (1) is preferably selected appropriately depending upon the sample.

It is preferred that the Step (X1) includes the following Steps (Xa) to (Xd).

(Xa) the step of performing data processing of a near infrared absorption spectrum (measurement wave number regions are 5990 to 5490 cm$^{-1}$ and 5000 to 4480 cm$^{-1}$) of two or more kinds of skins in which at least one of the degree of skin damage caused by UV light and the degree of physiological aging of a skin is known, if required.

(Xb) the step of creating a matrix from at least one of a spectrum value for each of divided wave numbers, a UV irradiation amount to a skin, a UV irradiation site, an age in week (a mouse, etc.), and an actual age of the near infrared absorption spectrum or the near infrared absorption spectrum that is subjected to data processing (hereinafter, which will be referred to as a "spectrum" collectively).

(Xc) the step of deriving two optimum principal components by subjecting the matrix created in the (Xb) to perform multivariate analysis.

(Xd) the step of obtaining a relative relationship of each sample, assuming that one of the two principal components derived in the (Xc) is a first axis and the other is a second axis, thereby obtaining a correlation between: at least one of the degree of skin damage caused by UV light and the degree of physiological aging of a skin; and the near infrared absorption spectrum.

The wave number regions of the near infrared absorption spectrum or the near infrared absorption spectrum that is subjected to data processing in the Step (Xa) are 5990 to 5490 cm$^{-1}$ and 5000 to 4480 cm$^{-1}$. It is assumed that the near infrared absorption spectra in the wave number regions exactly capture the structural changes in a protein and the changes in collagen, elastin, skin thickness, ceramide, and the like, and exactly reflect the degree of skin damage caused by UV light and the degree of physiological aging of a skin (see FIG. 1). Even the examples described later show that the analysis results of the multivariate analysis of the near infrared absorption spectra in the wave number regions or the spectra that are subjected to data processing, and the degree of skin damage caused by UV light and the degree of physiological aging of a skin have an adequate correlation.

The data processing of the near infrared absorption spectrum in the Step (Xa) includes pre-processing and transformation. The pre-processing includes autoscale, mean center, range scale, variance scale, and the like. The transformation includes a first differential, a multi-differential (including a secondary differential), standard normal variant (SNV), multiplicative scatter correction (MSC), normalize, smoothing, subtract, Log10, multiply, baseline correct, and the like.

The data processing in the Step (Xa) includes preferably a secondary differential, more preferably standard normal variant (SNV) and a secondary differential, and much more preferably mean center, standard normal variant (SNV), and a secondary differential. Due to these processings, the correction of variation in individual difference, the influence by noise and an outlier can be excluded, whereby the quality of data can be enhanced.

In any case, the data processing is preferably performed so that two principal components derived in the Step (Xc) from the matrix created in a Step (Xb) described later shows more exact correlation with the degree of skin damage caused by UV light and the degree of physiological aging of a skin.

A column of the matrix created in the Step (Xb) is a spectrum value for each of divided wave numbers of the infrared absorption spectrum of each skin. The spectrum value means an absorbance in the case of a near infrared absorption spectrum that is not transformed, and a differential value of an absorbance in the case of a differentiated spectrum.

Herein, although it is preferred that the spectrum is divided for a constant wave number, the wave number is not particularly limited. The spectrum is divided generally for a wave number of 2 to 16 $cm^{-1}$, preferably 4 to 8 $cm^{-1}$ (4 or 8 $cm^{-1}$ if the resolution is 4 $cm^{-1}$), and more preferably 4 $cm^{-1}$. Further, the spectrum value of a spectrum for each of divided wave numbers may be set to be each average value.

A column in the matrix created in the Step (Xb) is at least one of skin damage caused by UV light and the degree of physiological aging of two or more kinds of skins (skins in which at least one of the degree of damage caused by UV light and the degree of physiological aging is known) measured for spectra in the Step (Xa). Herein, at least one of the degree of skin damage caused by UV light and the degree of physiological aging of a skin may be shown by at least one difference in the degree and state of the processing treated to the skin. At least one difference in the degree and state of the processing treated to the skin means that at least one of a UV irradiation amount, a UV irradiation site, an age in week of a living body, an actual age, and the like.

That is, with respect to each spectrum obtained from two or more kinds of skins in which at least one of the degree of skin damage caused by UV light and the degree of physiological aging is known, a matrix is created from the spectrum value for each of the divided wave numbers and the data regarding at least one of a UV irradiation amount to a skin, a UV irradiation site, an age in week (a mouse, etc.), and an actual age. For example, matrices as shown in the following Table 1 are created. The number of samples is preferably 20 or more, and more preferably 40 or more.

TABLE 1

| | Wave number ($cm^{-1}$) | | | | | |
|---|---|---|---|---|---|---|
| Data | 5990-5982 | 5982-5974 | 5974-5966 | ... | ... | 4488-4480 |
| 1 | 0.13 | 0.23 | 0.13 | ... | 0.88 | 0.50 |
| 2 | 0.32 | 0.32 | 0.34 | ... | 0.32 | 0.40 |
| 3 | 0.34 | 0.34 | 0.22 | ... | 0.34 | 0.70 |
| . | 0.22 | 0.22 | 0.60 | ... | 0.50 | 0.44 |
| n | 0.12 | 0.14 | 0.30 | ... | 0.35 | 0.37 |

*Each value in the table is an absorbance (or a secondary differential value) of a near infrared spectrum.
*The data refer to samples having different conditions of an age, a site, and a UV irradiation amount of a human being, a mouse or the like.

As the algorithm of the multivariate analysis in the Step (Xc), a principal component analysis (PCA) method, a soft independent modeling of class analogy (SIMCA) method, or a k nearest neighbors (KNN) method is preferably used, and the principal component analysis method or the SIMCA method is more preferred. The multivariate analysis can use any known methods without any particular limit, in addition to the principal component analysis method, SIMCA method, KNN method, and the like.

The multivariate analysis is a procedure for associating the chemical characteristics such as spectral data and the specific values such as a physical property by the metrological processing, and analyzing the relationship.

The principal component analysis method is a method of selecting two components to be an object (which in this case means physiological aging and damage caused by UV light) from principal components contributing to the fluctuation, analyzing the second principal component axis perpendicular with respect to the first principal component axis, and comparing and estimating the physical properties in pattern changes in coordinates formed by the two principal component axes, in the case of analyzing the relationship between the appearing spectral pattern of a variable such as an absorbance and the specific value of a sample in continuous changes in factors such as a wave number in a particular sample or the like.

The SIMCA method and KNN method are those which have a function of estimating and classifying an unknown sample in addition to an analysis function. In recent years, some principal component analysis methods have an estimation function. The statistical processing such as the principal component analysis method or the SIMCA method, and the KNN method can be performed, using commercially available software. As such software for statistical processing, for example, software such as "Pirouette" (registered trademark) available from GL Sciences Inc., "MATLAB" (registered trademark) available from CYBERNET SYSTEMS CO., LTD., "Unscrumbler II" available from Yokogawa Electric Corporation, "SIMCA" available from SEPANOVA can be mentioned.

The multivariate analysis shows that two principal components derived from the matrix are unrelated to each other, i.e., vectors are perpendicular to each other. The two principal components have a correlation with the degree of skin damage caused by UV light and the degree of physiological aging of a skin.

Further, if the third component is obtained if required, the damage state of a skin other than the degree of damage caused by UV light and the degree of physiological aging can also be diagnosed. Examples of the damage state of a skin other than the degree of damage caused by UV light and the degree of physiological aging include morphologic abnormality, transformation of a connective tissue component, and the like.

The Step (Xd) is a step of obtaining the relative relationship of each sample, with at least two principal components obtained in the Step (Xc) being axes.

For example, a plane scatter diagram with two principal components being axes is created, and the relative relationship of each sample can be obtained from the positional relationship of a plot corresponding to each sample. By obtaining the relative relationship of each sample, the correlation between at least one of the degree of skin damage caused by UV light and the degree of physiological aging of a skin, and the near infrared absorption spectrum of a skin can be obtained. Further, the relative relationship of each sample thus obtained may be grouped on the basis of at least one of the degree of skin damage caused by UV light and the degree of physiological aging of a skin. The grouping can be performed using, for example, an algorithm of the SIMCA method.

Figure 5:
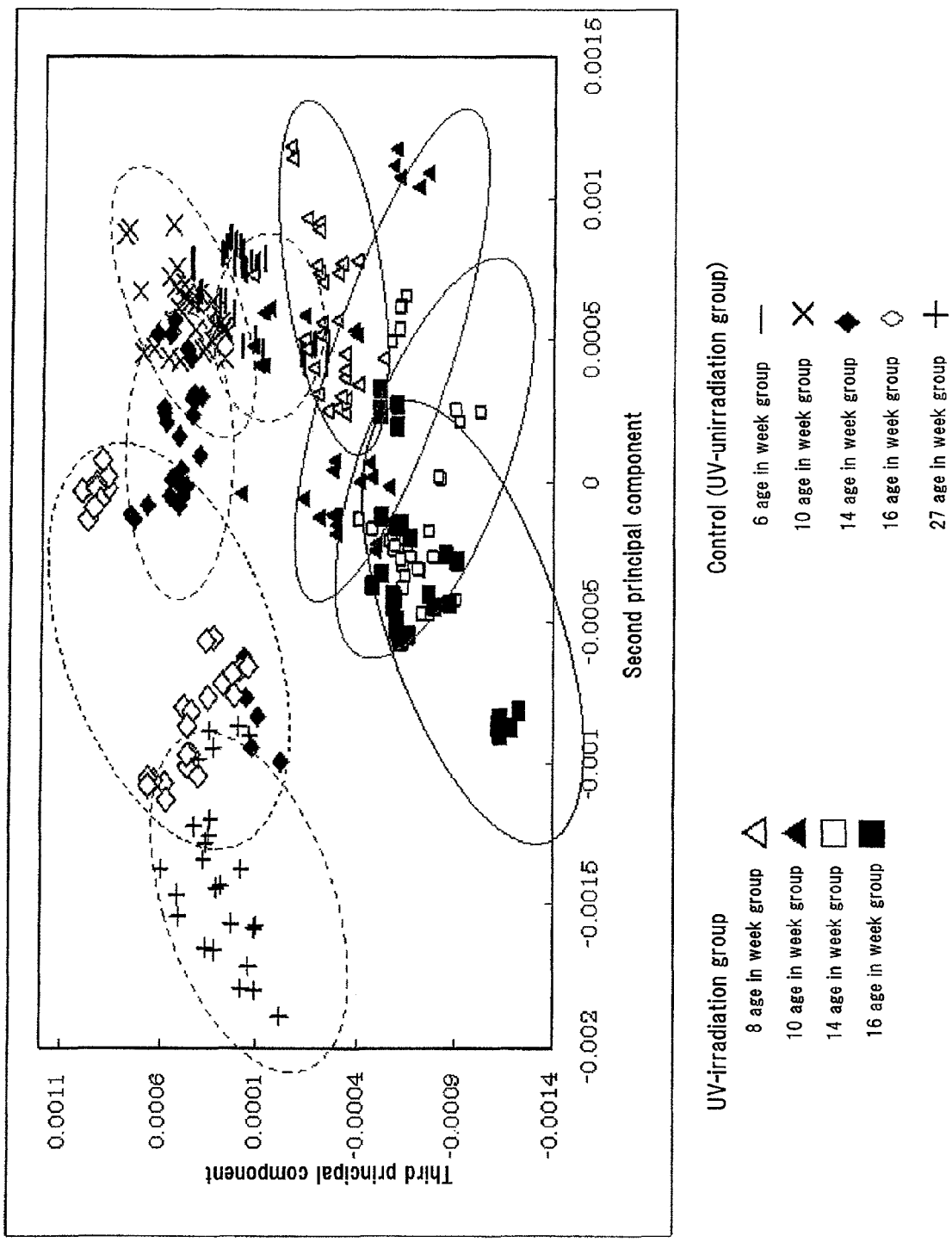
FIG. 5 is a diagram displaying a relationship between the degree of damage caused by UV light and the degree of physiological aging, which are results of a skin of a hairless mouse shown in Example 1, using a scatter diagram and a density ellipse.

Specifically, in the analysis results of the multivariate analysis, one (for example, one of the two principal components is assumed to be a component A) of at least two principal components thus obtained shows the relative relationship with respect to the degree of skin damage caused by UV light, and the other principal component (for example, the other of the two principal components is assumed to be a component B) shows the relative relationship with respect to the degree of physiological aging of a skin (for example, see FIG. 5). That is, the principal component axis of the component A shows the degree of damage caused by UV light, and the principal component axis of the component B shows the degree of physiological aging. By seeing the relative relationship on an axis of the component A between an uninjured skin (i.e., skin not irradiated with UV light) and a skin irradiated with UV light, the relative relationship between the degree of damage caused by UV light and the spectrum can be obtained.

Similarly, by seeing the relative relationship regarding an axis of the component B between an uninjured skin (i.e., a new skin) and the skin having physiological aging, the relative relationship between the degree of physical aging and the spectrum can be obtained.

Further, the degree to which the change in a spectrum value in each wave number region affects in the change shown by a principal component axis is understood from a loading plot (plot of a factor load amount by multivariate analysis) regarding spectra in various wave number regions (see FIG. 1). Thus, at least one of the degree of skin damage caused by UV light and the degree of physiological aging of a skin can be taken as a specific chemical change (peak change).

On the other hand, the method of estimating of the present invention includes the steps of:

(Y1) obtaining a correlation between at least one of an epidermal thickness and a dermal thickness of a skin and a near infrared absorption spectrum in a particular wave number region of the skin, from analysis results of multivariate analysis of the near infrared absorption spectrum in the particular wave number region in measurement wave number regions of 6850 to 6620 $cm^{-1}$, 6540 to 5990 $cm^{-1}$, 5240 to 5180 $cm^{-1}$, 5030 to 4980 $cm^{-1}$, 4760 to 4720 $cm^{-1}$, and 4650 to 4610 $cm^{-1}$, or 6940 to 6850 $cm^{-1}$, 6710 to 6540 $cm^{-1}$, 6250 to 6170 $cm^{-1}$, 5130 to 5080 $cm^{-1}$, 4950 to 4850 $cm^{-1}$, 4760 to 4690 $cm^{-1}$, and 4670 to 4610 $cm^{-1}$ of two or more kinds of skins in which at least one of an epidermal thickness and a dermal thickness of a skin is known;

(Y2) obtaining a near infrared absorption spectrum in a particular wave number region of a skin in which at least one of an epidermal thickness and a dermal thickness of the skin to be estimated is unknown; and (Y3) estimating at least one of the epidermal thickness and the dermal thickness of the skin from the near infrared absorption spectrum in the particular wave number region obtained in the Step (Y2) based on the correlation obtained in the Step (Y1).

The near infrared absorption spectrum of a skin in the Step (Y1) can be obtained by any suitable method in the same way as in the Step (X1).

Further, the multivariate analysis in the Step (Y1) means the construction or the like of a model (herein, an estimation model or a calibration line) for clarifying the relationship between samples (actually measured value and an estimated value of at least one of an epidermal thickness and a dermal thickness of a skin in the present invention) by calculating a similarity or the like based on a plurality of observation values (herein, near infrared absorption spectrum data) in the same way as in the Step (X1). It is preferred that the multivariate analysis method in the Step (Y1) is appropriately selected depending upon the sample.

It is preferred that the Step (Y1) includes the following Steps (Ya) to (Yd).

(Ya) the step of performing deta processing of the near infrared absorption spectra (measurement wave number regions are 6850 to 6620 $cm^{-1}$, 6540 to 5990 $cm^{-1}$, 5240 to 5180 $cm^{-1}$, 5030 to 4980 $cm^{-1}$, 4760 to 4720 $cm^{-1}$, and 4650 to 4610 $cm^{-1}$, or 6940 to 6850 $cm^{-1}$, 6710 to 6540 $m^{-1}$, 6250 to 6170 $cm^{-1}$, 5130 to 5080 $cm^{-1}$, 4950 to 4850 $cm^{-1}$, 4760 to 4690 $cm^{-1}$, and 4670 to 4610 $cm^{-1}$) of two or more kinds of skins in which at least one of the epidermal thickness and the dermal thickness is known, if required.

(Yb) the step of creating a matrix from a spectrum value of each of divided wave numbers and a thickness of a skin (at least one of an epidermis and a dermis), and at least one of a UV irradiation amount of a skin, a UV irradiation site, an age in week (a mouse, etc.), and an actual age of the above near infrared absorption spectrum or the above spectrum subjected to data processing (hereinafter, which will be referred to as a "spectrum" collectively).

(Yc) the step of deriving an estimated value of a thickness of a skin (at least one of an epidermis and a dermis) by subjecting the matrix created in the (Yb) to multivariate analysis.

(Yd) the step of obtaining a relative relationship (calibration line) of each sample, assuming that actually measured values of two or more kinds of skins in which at least one of an epidermal thickness and a dermal thickness of a skin is known is a first axis, and an estimated value of a thickness of the skin (at least one of an epidermis and a dermis) is a second axis, thereby obtaining a correlation between at least one of the epidermal thickness and the dermal thickness of the skin and the near infrared absorption spectrum of the skin.

Figure 2:
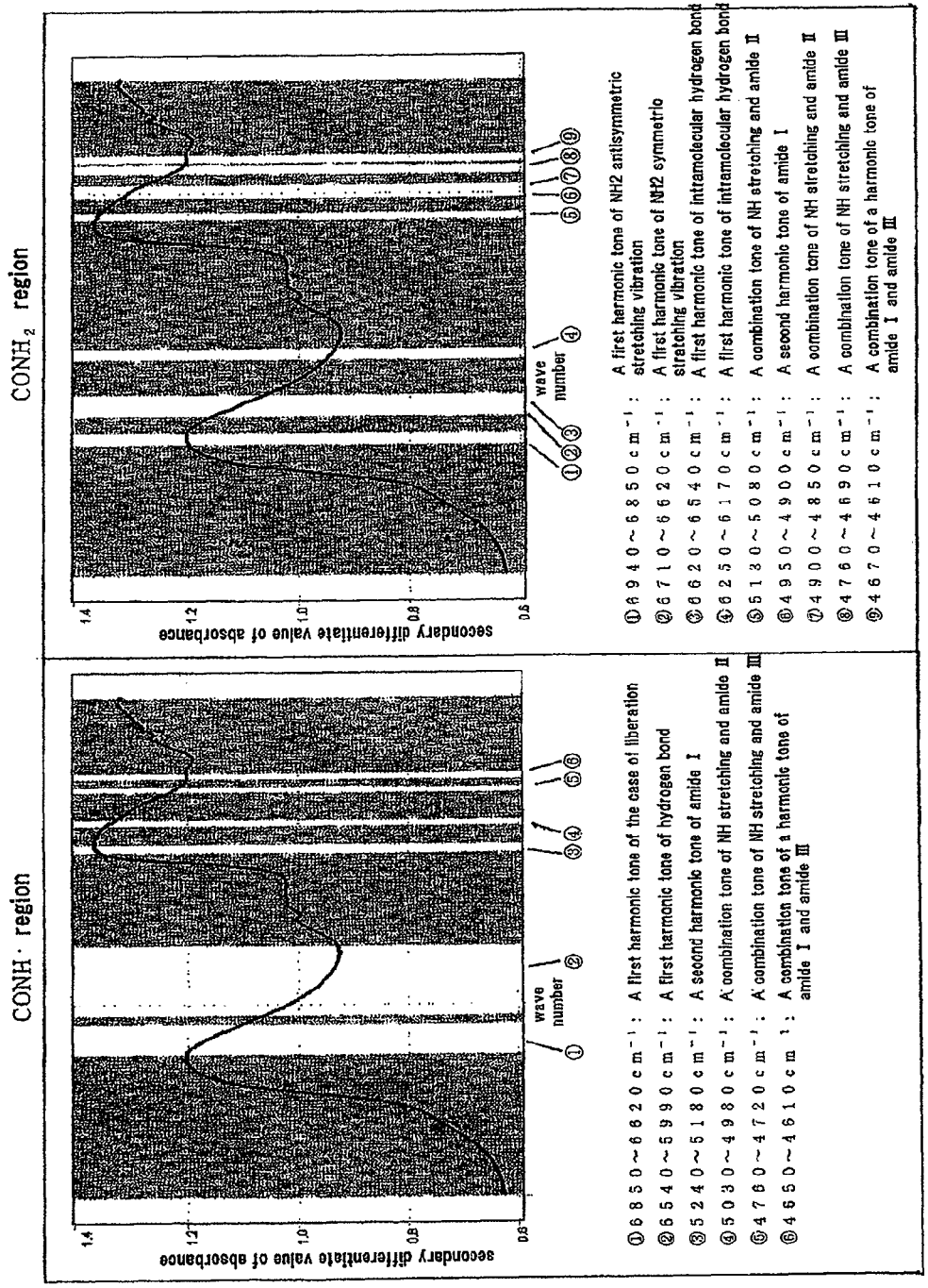
FIG. 2 is a diagram showing a wave number region of a near infrared absorption spectrum representing the characteristics of an amide bond (CONH) and amide (CONH$_2$).

The wave number region of the near infrared absorption spectrum or the near infrared absorption spectrum that is subjected to data processing in the Step (Ya) is 6850 to 6620 $cm^{-1}$, 6540 to 5990 $cm^{-1}$, 5240 to 5180 $cm^{-1}$, 5030 to 4980 $cm^{-1}$, 4760 to 4720 $cm^{-1}$, and 4650 to 4610 $cm^{-1}$, or 6940 to 6850 $cm^{-1}$, 6710 to 6540 $cm^{-1}$, 6250 to 6170 $cm^{-1}$, 5130 to 5080 $cm^{-1}$, 4950 to 4850 $cm^{-1}$, 4760 to 4690 $cm^{-1}$, and 4670 to 4610 $cm^{-1}$ (see FIG. 2).

The near infrared absorption spectra in the above wave number regions are conjectured to reflect the structural characteristics of amide bond characteristics, i.e., an amide bond (CONH) or amide ($CONH_1$), and the characteristics thereof are conjectured to be related to the thickness of a skin (at least one of an epidermis and a dermis). That is, in the case of the amide bond (CONH), the above wave number regions are conjectured to show a first harmonic tone of the case of liberation, a first harmonic tone of a hydrogen bond, a second harmonic tone of amide I, a combination tone of NH stretching and amide II, a combination tone of NH stretching and amide III, and a combination tone of a harmonic tone of amide I and amide III. Further, in the case of amide ($CONH_2$), the wave number regions are conjectured to show a first harmonic tone of $NH_2$ antisymmetric stretching vibration, each first harmonic tone of $NH_2$ symmetric stretching vibration and an intramolecular hydrogen bond, a first harmonic tone of an intermolecular hydrogen bond, a combination tone of NH stretching and amide II, a second harmonic tone of amide I, a combination tone of NH stretching and amide II, a combination tone of NH stretching and amide III, and a combination tone of a harmonic tone of amide I and amide III. This is also supported by the examples (described later), in which the coefficient of correlation of an actually measured value and an estimated value (calibration line) of a thickness of a skin (at least one of an epidermis and a dermis) in the regression analysis results using partial least squares (PLS) method of the spectra in the above wave number regions is very large.

The data processing in the Step (Ya) includes the pre-processing and transformation similar to those in the Step (Xa). Further, it is preferred that the data processing in the Step (Ya) includes a secondary differential in the same way as in the Step (Xa).

In any case, it is preferred that the data processing is performed so that an estimated value of a thickness of a skin (at least one of an epidermis and a dermis) derived in the Step (Yc) from the matrix created in Step (Yb) described later shows a high correlation with the actually measured value.

In the matrix created in the Step (Yb), a spectrum value for each of divided wave numbers and a thickness of a skin (at least one of an epidermis and a dermis) of the similar infrared absorption spectrum of each skin as that in the (Xb) are used. As the thicknesses of the epidermis and the dermis of the skin, values actually measured using various kinds of skin samples prepared by the following method may be used.

The number of samples is preferably 20 or more, and preferably 40 or more.

TABLE 2

| Data | Thickness | Wave number (cm$^{-1}$) | | | | | |
|---|---|---|---|---|---|---|---|
| | | 6850-6842 | 6842-6834 | 6834-6826 | ... | ... | 4618-4610 |
| 1 | 58.0 | 0.13 | 0.23 | 0.13 | ... | 0.88 | 0.50 |
| 2 | 77.2 | 0.32 | 0.32 | 0.34 | ... | 0.32 | 0.40 |
| 3 | 47.3 | 0.34 | 0.34 | 0.22 | ... | 0.34 | 0.70 |
| . | 89.3 | 0.22 | 0.22 | 0.60 | ... | 0.50 | 0.44 |
| n | 39.4 | 0.12 | 0.14 | 0.30 | ... | 0.35 | 0.37 |

* Each value in the table is an absorbance (or a secondary differential value) of a near infrared spectrum.
* The data refer to samples having different conditions such as an age, a site, and a UV irradiation amount of a human being, a mouse, or the like.

Figure 3:
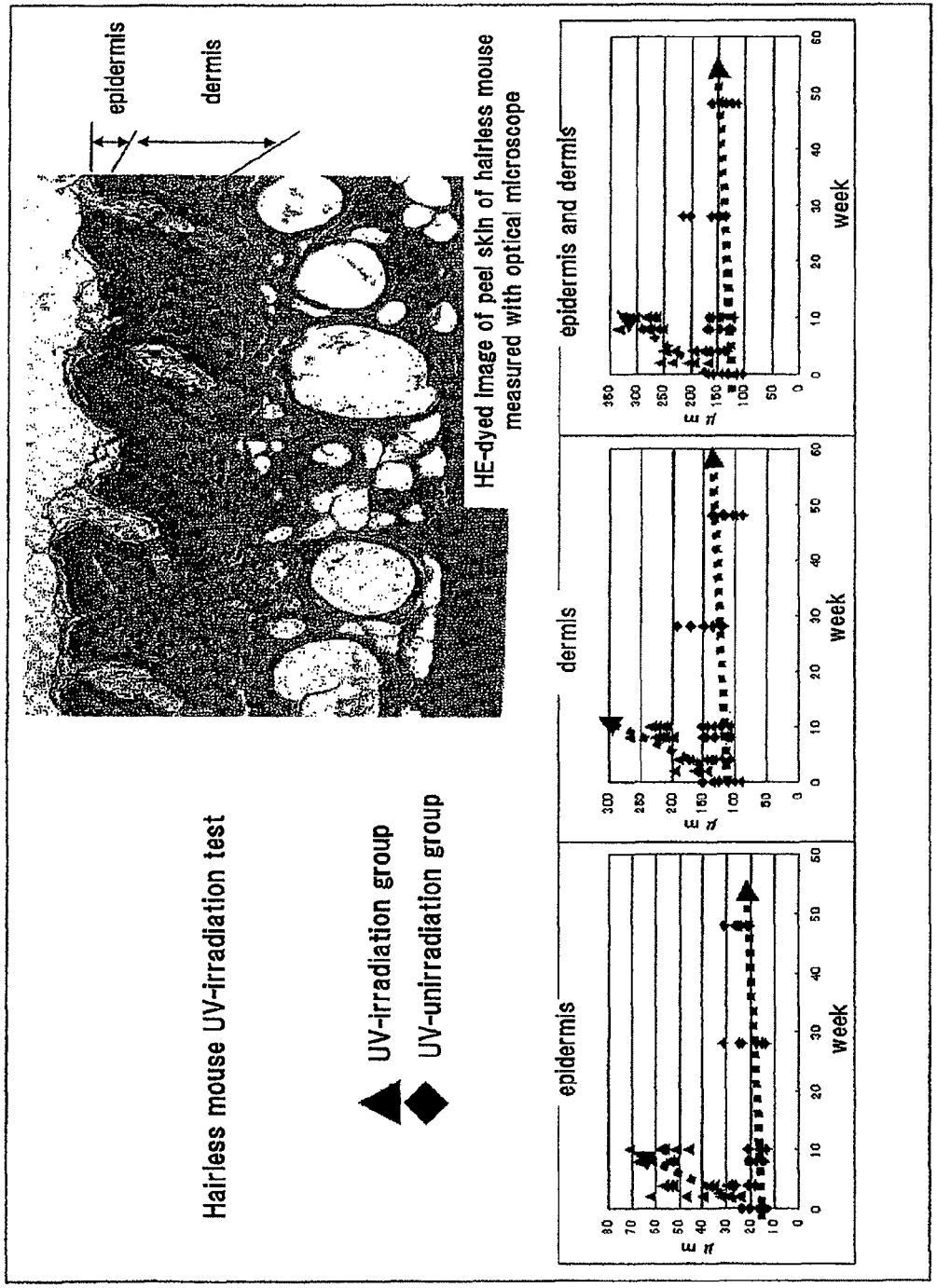
FIG. 3 is a diagram showing an HE-dyed image of a peeled skin segment and measurement values of an epidermis and a dermis of a skin sample group of a hairless mouse.

For example, in the case of a hairless mouse, a skin is peeled from a back portion to prepare a skin segment of 5 mm×5 mm. Then, the skin segment is fixed with 10% neutral buffer formalin to produce an HE-dyed tissue sample, and the thickness of the skin is measured with an optical microscope. FIG. 3 shows an HE-dyed image of the peeled skin, and examples of thickness measurement values of an epidermis, a dermis, and a skin (an epidermis and a dermis). FIG. 3 shows that the influence of an age in week with respect to the thickness of the epidermis and the dermis is very small in the UV-unirradiated group, and various values of 1 to 5 times those of the UV-unirradiated group are exhibited with respect to the thickness of the epidermis and the dermis in the UV-irradiated group. Thus, it is understood that the values of the thicknesses of the epidermis and the dermis obtained from an HE-dyed image or the like can be used preferably when the method of the present application is carried out.

Figure 4:
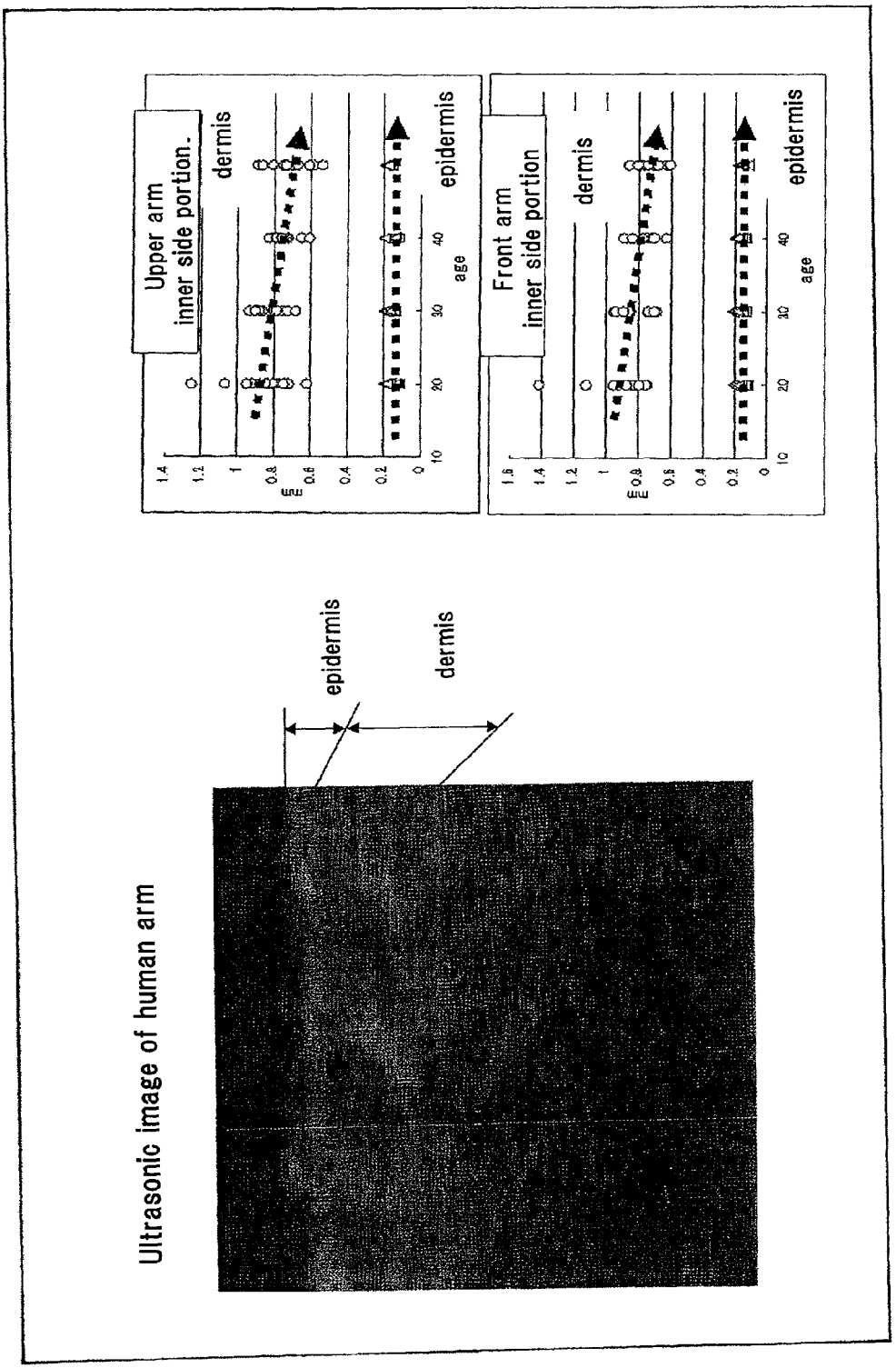
FIG. 4 is a diagram showing an ultrasonic image, and measurement values of an epidermis and a dermis of a skin sample group of upper arm and front arm portions of a human arm.

Further, for example, in the case of a human being, ultrasonic measurement (for example, an ultrasonic diagnostic apparatus UX-02, etc., manufactured by Rion Co., Ltd.) is performed using a site difference by the presence/absence of exposure to UV light, i.e., a covered trunk portion (an upper arm inner side, a back, an abdomen, or the like) and an exposed site (a front arm outer side, a face, or the like), and the value of a thickness of a skin (at least one of an epidermis and a dermis) obtained from the ultrasonic image may be used. FIG. 4 shows an ultrasonic image, and examples of measurement values of the thickness of each epidermis and dermis in an upper arm outer side portion and a front arm inner side portion. From FIG. 4, various values such as a change in thickness of a dermis due to aging are obtained. According to the invention of the present application, it is understood that the value of the thickness of a skin obtained from the ultrasonic image or the like can be used preferably.

In the matrix created in the Step (Yb), at least one of a UV irradiation amount, a UV irradiation site, an age in week of a living body (mouse, etc.), and an actual age of two or more kinds of skins (skins in which the thickness of at least one of an epidermis and a dermis is different) measured for spectrum in the Step (Ya) can be used.

That is, a matrix is created from a spectrum value for each of divided wave numbers and the thickness of at least one of an epidermis and a dermis, and at least one of a UV irradiation amount of a skin, a UV irradiation site, an age in week of a living body (mouse, etc.), and an actual age, with respect to each spectrum obtained from two or more kinds of skins in which the thickness of at least one of the epidermis and the dermis is different. For example, matrices as shown in the following Table 2 are created.

As an algorithm of the multivariate analysis (regression analysis) in the Step (Yc), a partial least squares (PLS) method or a principal component regression (PCR) analysis method is preferably used. The reason for this is as follows. The final object of the regression analysis is to construct an estimation model for estimating the related specific values (herein, the thickness of at least one of an epidermis and a dermis of a skin). In the case of using a measured value obtained by a spectrophotometer as a explanatory variable so as to estimate continuous specific values in the model, the PLS or the PCR is very advantageous in terms of the high estimation precision and exactness, the identification of an outlier, the optimization of the model, and the like, compared with simple linear regression analysis and multiple regression analysis (MRA). Further, the estimation model can be optimized to a model with a high estimation precision by updating a database (DB) by the addition of skin samples.

The regression analysis of the PLS and the PCR can be performed using commercially available software. Examples of such software include "Pirouette" (registered trademark) available from GL Sciences Inc., "MATLAB" (registered trademark) available from CYBERNET SYSTEMS CO., LTD., and "Unscrumbler II" available from Yokogawa Electric Corporation, or the like.

The Step (Yd) is a step of constructing an estimation model (calibration line) from an estimated value of the thickness of a skin obtained in the Step (Yc), and obtaining a correlation between at least one of an epidermal thickness and a dermal thickness of a skin and a near infrared absorption spectrum value of the skin. More specifically, by obtaining a relative relationship of each sample, assuming that actually measured values of two or more kinds of skins in which at least one of an epidermal thickness and a dermal thickness of a skin is known is a first axis, and an estimated value of at least one of the epidermal thickness and the dermal thickness of the skin is a second axis, a correlation (calibration line) between at least one of the epidermal thickness and the dermal thickness of the skin and the near infrared absorption spectrum of the skin can be obtained.

For example, if a plane scatter diagram composed of two axes of an actually measured value and an estimated value of at least one of an epidermal thickness and a dermal thickness of a skin is created, an approximate estimated value of at least one of an epidermal thickness and a dermal thickness of a skin, precision, characteristics of skin samples (e.g., a UV irradiation amount, a site, an age in week, or an actual age), and the like can be conjectured by the positional relationship of a plot of each sample and a coefficient of correlation.

The Steps (X2) and (Y2) include the step of obtaining a near infrared absorption spectrum of: a skin in which at least one of the degree of skin damage caused by UV light and the degree of physiological aging of a skin that are to be determined is unknown; or a skin in which at least one of an epidermal thickness and a dermal thickness of a skin that are to be estimated is unknown.

It is preferred that the near infrared absorption spectra in the Steps (X2) and (Y2) be obtained by measurement by the same method or apparatus as that in the measurement of the near infrared absorption spectra in the Steps (X1) and (Y1). Further, it is preferred that the obtained near infrared absorption spectra are subjected to data processing in the same way as in the Steps (X1) and (Y1). Hereinafter, the Step (X2) and (Y2) may be referred to as the Step (2) collectively.

The Step (X3) includes the step of determining at least one of the degree of skin damage caused by UV light and the degree of physiological aging of a skin from the near infrared absorption spectrum obtained in the Step (X2) based on the correlation obtained in the Step (X1). Further, the Step (Y3) includes the step of estimating at least one of an epidermal thickness and a dermal thickness of a skin from the near infrared absorption spectrum obtained in the Step (Y2) based on the correlation obtained in the Step (Y1). Hereinafter, the Step (X3) and the Step (Y3) may be referred to as Step (3) collectively.

The Step (3) is represented by the following [A] or [B].

[A] The spectrum data obtained in the Step (X2) is added to the matrix whose correlation is obtained in the Step (X1), and the multivariate analysis is performed in the same way as in the Step (X1), whereby at least one of the degree of skin damage caused by UV light and the degree of physiological aging of a skin, which are to be determined, is determined (principal component analysis method).

Alternatively, the spectrum data obtained in the Step (X2) is applied to the model obtained from the correlation obtained in the Step (X1), whereby at least one of the degree of skin damage caused by UV light and the degree of physiological aging of a skin, which are to be determined, is determined (SIMCA or KNN method). That is, the analysis results of a skin in which the degree of damage caused by UV light and the degree of physiological aging are known and the analysis results of a skin in which the degree of damage caused by UV light and the degree of physiological aging are unknown are checked using the correlation with respect to axes of two principal components, whereby at least one of the degree of skin damage caused by UV light and the degree of physiological aging of the unknown skin can be determined. The relative relationship with respect to axes of two principal components can be represented, for example, on a plane scatter diagram having a first principal component and a second principal component as axes.

[B] The spectrum data obtained in the Step (Y2) is applied to the model obtained from the correlation obtained in the Step (Y1), whereby at least one of an epidermal thickness and a dermal thickness of a skin to be estimated is estimated. The spectrum data (matrix) whose correlation is obtained in the Step (Y1) is combined with the spectrum data obtained in the Step (Y2), and the regression analysis is performed in the same way as in the Step (Y1), whereby at least one of an epidermal thickness and a dermal thickness of a skin to be estimated is estimated. That is, in an estimation model (calibration line) of a skin in which at least one of an epidermal thickness and a dermal thickness of a skin is known, the analysis results of a skin in which at least one of an epidermal thickness and a dermal thickness of a skin is unknown is checked relatively, whereby at least one of an epidermal thickness and a dermal thickness of the unknown skin can be estimated. In the above estimation, an estimated value and estimation precision can be shown based on the correlation in the estimation model. The Step (Y3) can be performed using software of regression analysis.

In the Step (X3), the analysis results of a unknown skin using the relative relationship with respect to axes of a component A (one of two principal components) and a component B (the other one of two principal components) obtained from the analysis results of a skin in which at least one of the degree of damage caused by UV light and the degree of physiological aging is known are checked, whereby at least one of the degree of damage caused by UV light and the degree of physiological aging of the unknown skin can be estimated. The relative relationship with respect to the axes of the components A and B can be expressed, for example, on a plane scatter diagram having the components A and B as axes.

Further, in the Step (Y3), in an estimation model (calibration line) of a skin in which at least one of an epidermal thickness of a skin and a dermal thickness of a skin is known, the relative relationship of the analysis results of the unknown skin is checked, whereby at least one of an epidermal thickness and a dermal thickness of the unknown skin can be estimated. In the estimation, an estimated value and estimation precision can be shown based on the correlation in the estimation model.

The degree of skin damage caused by UV light and the degree of physiological aging of a skin can be evaluated with time using the method of the present invention. As a result, the determination results can be used for determining the necessity of the treatment and care of a skin by cosmetics, medicine, operation, or beauty treatment, or the like. Further, the evaluation results can also be used for determining the effects of the treatment and care. Further, based on these determination results, it is possible to select desired cosmetics and the like and provide advice thereof, for example, it is possible to use cosmetics mixed with a UV inhibitor and a skin-lightening agent in the case where the degree of damage caused by UV light is high, and to use cosmetics mixed with a humectant and an anti-aging agent in the case where the degree of physiological aging is high.

Further, whether a skin changes, i.e., the thicknesses of an epidermis and a dermis change, and the change increases or decreases can be monitored with time using the method of the present invention. Further, the monitoring results can be used for determining the necessity of the treatment and care of a skin by cosmetics, medicine, operation, beauty treatment or the like, determining the effects of the treatment and care, or selecting of desired cosmetics and providing advice and the like. For example, in the case where the thickness of the evaluated skin (one of an epidermis and a dermis) is biased statistically compared with an average value of an actual age and a site, it is conjectured that the hypertrophy of an epidermis caused by the abnormal function of a skin tissue and an undesirable state caused by abnormality or the like of an extracellular matrix (collagen, etc.) occur, whereby it is determined that the above treatment and care are necessary. Further, in the case where the thickness of the discriminated skin (one of an epidermis and a dermis) changes with time, it is determined that the treatment and care have effects thereto.

Further, the thickness of a skin (one of an epidermis and a dermis) is compared before and after the administration of cosmetics or before and after the performance of beauty treatment, and the effects of cosmetics and beauty treatment can be evaluated using the change as an index. For example, in the case where the thickness of a dermis is small, and the thickness of a dermis increases due to the use of cosmetics mixed with a collagen synthesis promoter, a collagen fiber bundle reconstruction agent, and the like, it can be evaluated that the cosmetics and beauty treatment have a wrinkle eliminating effect. Further, in the case where the thickness of an epidermis is large and the increase in an epidermis is suppressed by the use of cosmetics mixed with a turnover adjusting agent and the like, and the thickness of an epidermis decreases, it can be evaluated that the cosmetics have an epidermis hypertrophy suppressing function.

The method of the present invention does not have an object of treating or diagnosing a human being, and excludes the medical practice.

Hereinafter, the present invention will be described in detail by way of examples and the like. It should be noted that the examples and the like do not limit the scope of the present invention.

EXAMPLES

<Preparation of an Animal Skin Sample>

Hairless mice were used for an animal skin sample collection, and a UV-irradiated group and a UV-unirradiated group were set, whereby a sample collection having various kinds of skin conditions and skin thicknesses were prepared. As the UV-unirradiated group, 30 mice in total were set in which 6 mice were included in each of a 6-week-old group (hereinafter, which may be expressed as CT6W or UV-unirradiated #6W group), a 10-week-old group (hereinafter, which may be expressed as CT10W or UV-unirradiated #10W group), a 14-week-old group (hereinafter, which may be expressed as CT14W or UV-unirradiated #14W group), a 16-week-old group (hereinafter, which may be expressed as CT16W or UV-unirradiated #16W group), and a 27-week-old group (hereinafter, which may be expressed as CT27W or UV-unirradiated #27W group). Further, as the UV-irradiated group, 24 mice in total were set in which 6 mice were included in each of an 8-week-old group (hereinafter, which may be expressed as UV8W or UV-irradiated #8W group), a 10-week-old group (hereinafter, which may be expressed as UV10W or UV-irradiated #10W group), a 14-week-old group (hereinafter, which may be expressed as UV14W or UV-irradiated #14W group), and a 16-week-old group (hereinafter, which may be expressed as UV16W or UV-irradiated #16W group).

<UV Irradiation Condition>

Regarding the UV irradiation, after the hairless mice reached an age of 6 weeks, each hairless mouse was irradiated with 0.1 dose (J/cm$^2$) of energy per administration, three times a week. Thus, the 10-week-old group of the UV-irradiated group refers to the skin in which UV irradiation was conducted for 4 weeks after the mice reached an age of 6 weeks, and which was irradiated with UV light of 1.2 dose (J/cm$^2$) in an accumulation 12 times during 4 weeks.

<Preparation of a Human Skin Sample>

Three portions including a front arm outer side portion, a front arm inner side portion, and an upper arm inner side portion were set in 60 female subjects (15 for each generation) in twenties to fifties having no disease in the arm skin, and these three portions were allowed to stand for 20 minutes after washing. Such a condition was determined to a human skin sample collection.

<Measurement of a Near Infrared Absorption Spectrum of a Skin Sample>

The near infrared absorption spectrum of a skin sample obtained by the preparation of the skin sample was measured at 20° C. under a predetermined circumstance. Herein, considering the possibility that the treatment varied depending upon the portion of the skin, the near infrared absorption spectrum of each site of the three portions selected at random was measured. A Fourier-transform near infrared spectrophotometer VECTOR 22/N (manufactured by Bruker Optics) was used for measuring the near infrared absorption spectrum. As the measurement conditions, a diffuse reflection method using a fiber probe was used with a resolution being 8 cm$^{-1}$ and a measurement wave number being 8000 to 4000 cm$^{-1}$.

Example 1

In the near infrared absorption spectrum of the skin sample collection obtained from the skins of the hairless mice, data processing was performed with respect to the wave number regions of 5990 to 5490 cm$^{-1}$, and 5000 to 4480 cm$^{-1}$. Specifically, the mean center and standard normal variant (SNV) were performed, and thereafter, second derivation was performed.

The spectrum subjected to data processing was divided for each 4 cm$^{-1}$, and a spectrum value (a secondary differential value of an absorbance) for each of the divided spectrum was calculated. A matrix was created from the calculated secondary differential value of a spectrum value for each wave number and the contents of a treatment (the presence/absence of UV irradiation and the difference in an irradiation amount, and the difference in an age of week) with respect to the skin. The created matrix was subjected to principal component analysis. From the obtained analysis results, a plane scatter diagram was created assuming a second principal component as a first axis and a third principal component as a second axis (two components showing physiological aging and damage caused by UV light were selected, and set as a first axis and a second axis, respectively). The data processing and principal component analysis were performed using multivariate analysis software (Pirouette (registered trademark) Version 3.11; GL Sciences Inc.).

FIG. 5 shows a plane scatter diagram created from the obtained analysis results of the multivariate analysis. As shown in FIG. 5, it is understood that the results are categorized very clearly on the basis of the presence/absence of UV irradiation, the difference in an irradiation amount, and the difference in an age in week. Specifically, it is understood that the degree of physiological aging of the skin is higher toward the left direction on the first axis (abscissa axis). Further, it is understood that the degree of skin damage caused by UV light is higher toward the lower direction on the second axis (ordinate axis). It is understood that both the degree of skin damage caused by UV light and the degree of physiological aging of a skin are higher toward the lower left direction. Thus, it is understood that the degree of skin damage caused by UV light and the degree of physiological aging of the skin individually have a clear correlation with the analysis results of the multivariate analysis of the near infrared absorption spectrum of the skin.

Example 2

Figure 6:
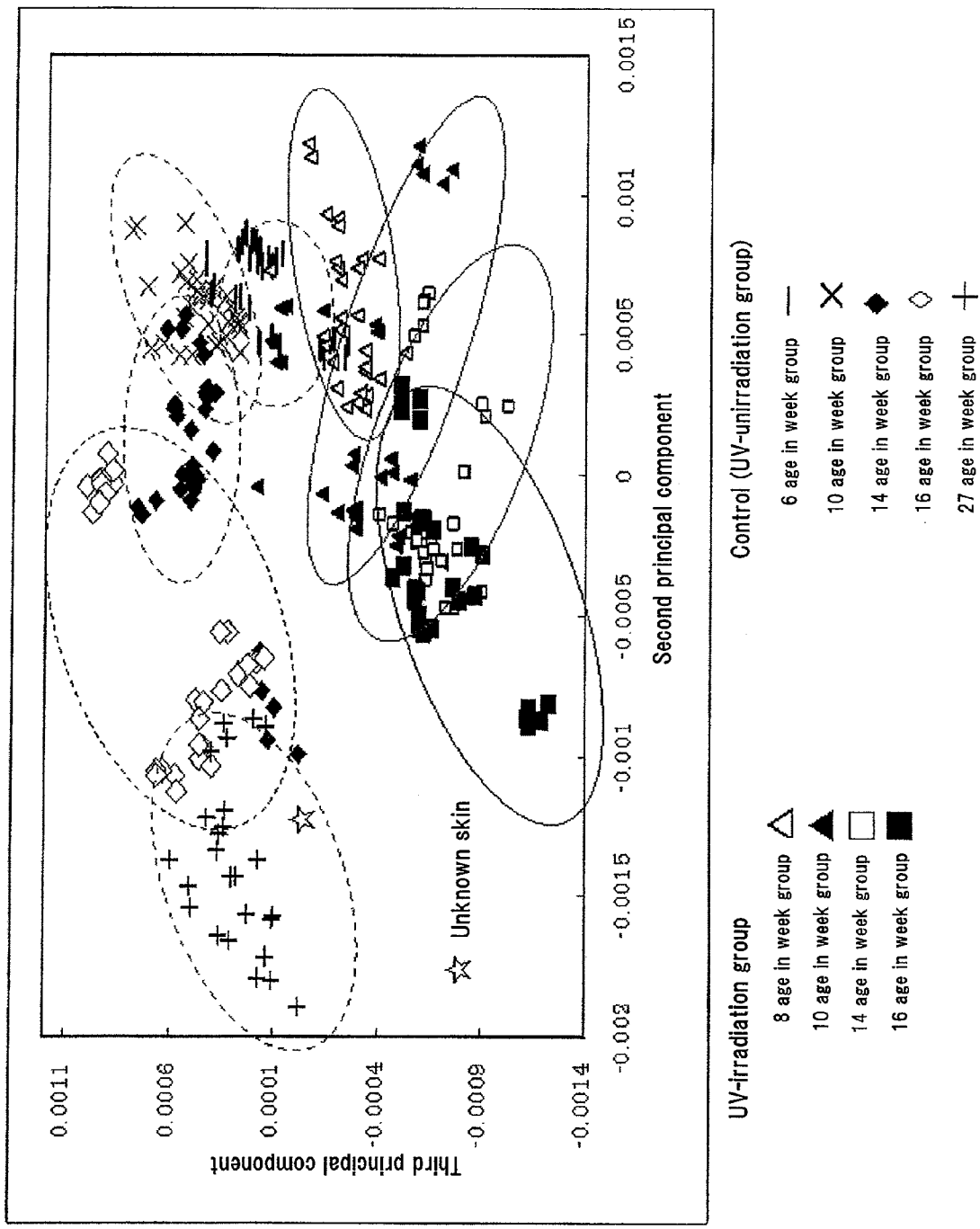
FIG. 6 is a diagram of results of a skin of a hairless mouse shown in Example 2, obtained by determining the degree of damage caused by UV light and the degree of physiological aging.

In Example 1, the near infrared absorption spectrum of a skin sample of a hairless mouse whose degree of skin damage caused by UV light and degree of physiological aging of a skin are unknown was added, and data processing was performed in the same procedure as that in Example 1 to create a matrix, whereby principal component analysis was performed. FIG. 6 is a scatter diagram created from the obtained results. As shown in FIG. 6, the respective sample groups having different contents of treatment were categorized clearly, and it was determined that, from a plot position of the result of the skin sample whose degree of damage caused by UV light and degree of physiological aging are unknown, this skin most corresponds to the UV-unirradiated 27-week-old group.

Example 3

Figure 7:
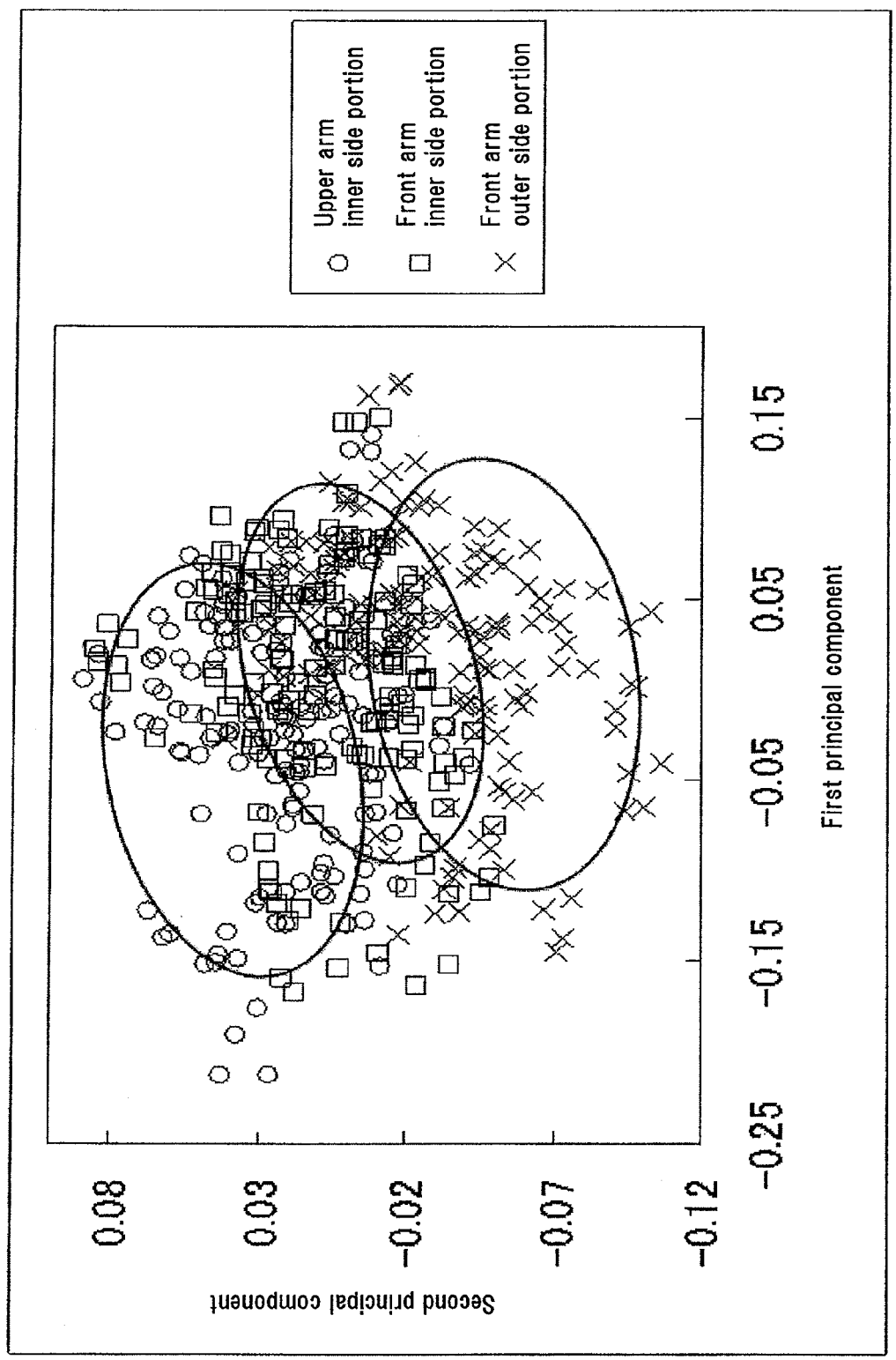
FIG. 7 is a diagram displaying a relationship between the degree of damage caused by UV light and the degree of physiological aging, which are results of a skin of a human being shown in Example 3, using a scatter diagram and a density ellipse.
Figure 8:
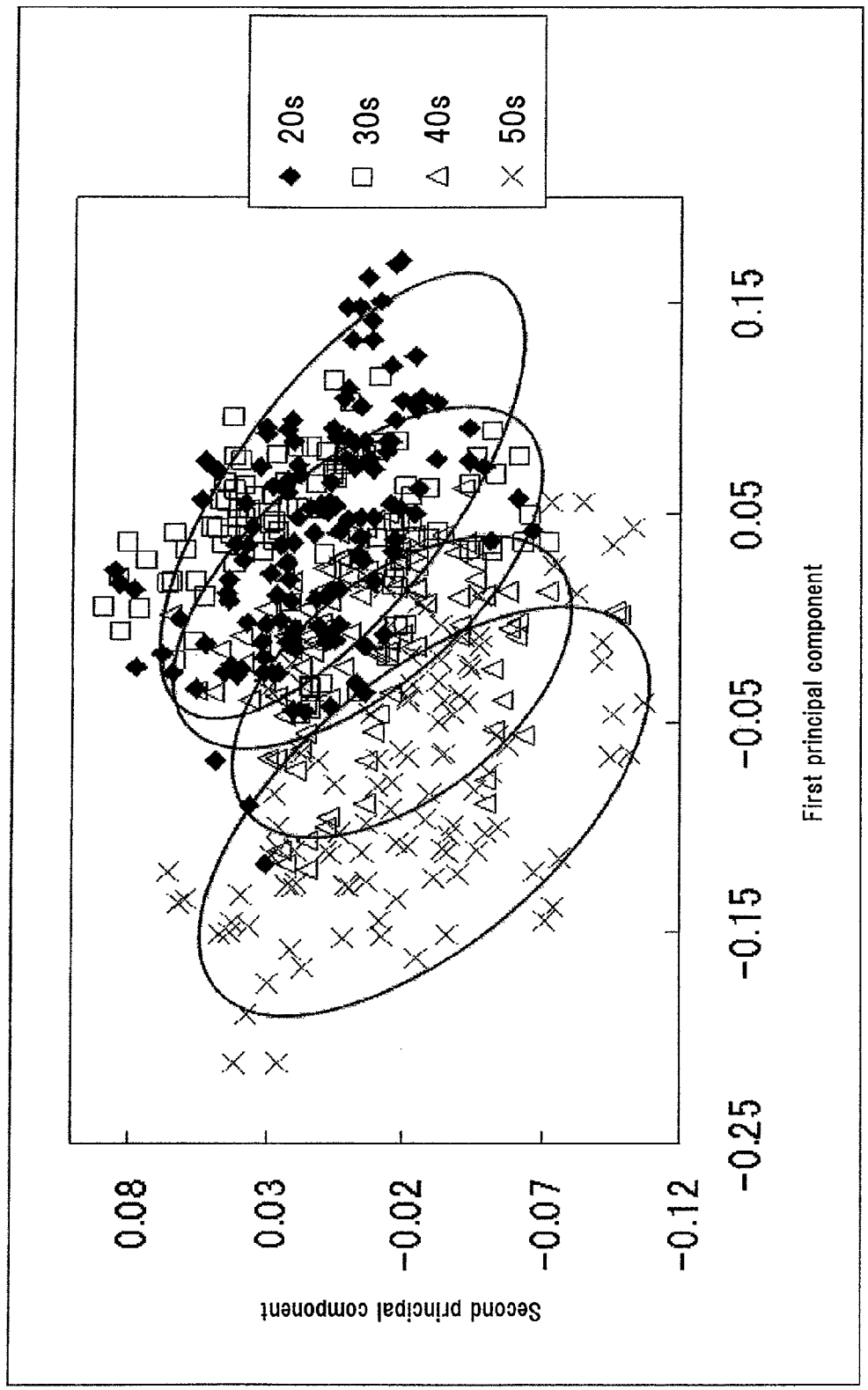
FIG. 8 is a diagram displaying a relationship between the degree of damage caused by UV light and the degree of physiological aging, which are results of the skin of a human being shown in Example 3, using a scatter diagram and a density ellipse.

The above human skin sample collection was subjected to measurement and analysis in the same way as in Example 1. Plane scatter diagrams were created from the obtained analysis results of the multivariate analysis assuming a first principal component as a first axis and a second principal component as a second axis. The created plane scatter diagrams are shown in FIGS. 7 and 8. A 95% density ellipse of a site-based category was obtained in FIG. 7, and a 95% density ellipse of an age-based category was obtained in FIG. 8. As shown in FIG. 7 or 8, it is understood that the results are categorized very clearly based on the site of an arm or the age. Specifically, the degree of physiological aging is higher toward the left direction on the axis (abscissa axis) of the first principal component, and the degree of damage caused by UV light is higher toward the lower direction on the axis (ordinate axis) of the second principal component. Thus, it is understood from FIG. 7 that the degree of damage caused by UV light is high in a front arm outer side portion that is exposed more, and the degree of damage caused by UV light is low in an upper arm inner side portion that is exposed less. Further, it is understood from FIG. 8 that the category is shifted toward the left direction and the degree of physiological aging proceeds from twenties to fifties. Thus, it is understood that the degree of human skin damage caused by UV light and the degree of physiological aging can be determined separately.

Comparative Example 1

Figure 9:
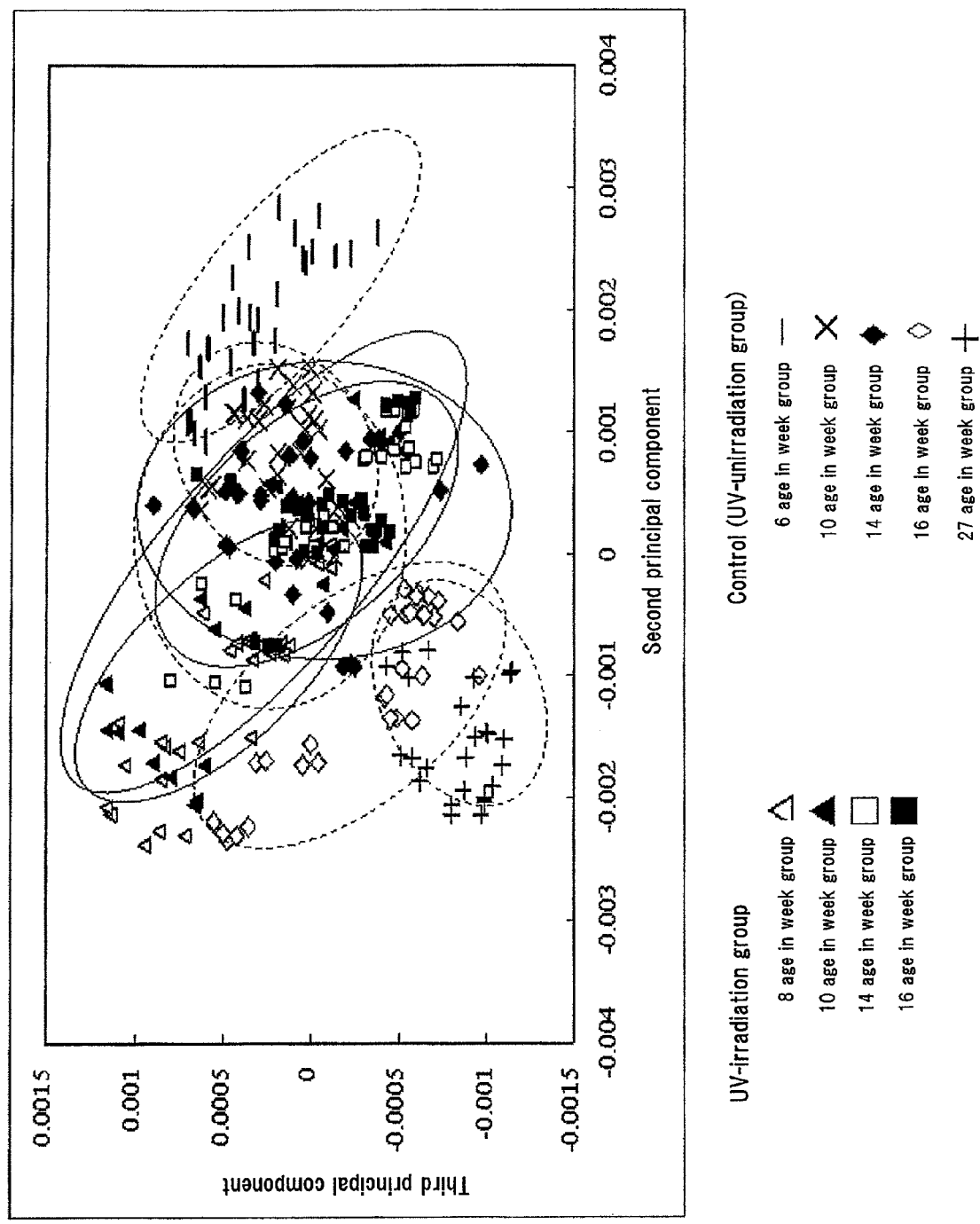
FIG. 9 is a diagram displaying a relationship between the degree of damage caused by UV light and the degree of physiological aging, which are results of a skin of a hairless mouse shown in Comparative Example 1, using a scatter diagram.

Scatter diagrams created from the results obtained by performing data processing and principal component analysis in wave number regions of 8000 to 4000 $cm^{-1}$ in Example 1 is shown in FIG. 9. As shown in FIG. 9, it is understood that the skins of hairless mice are not categorized depending upon the presence/absence of UV irradiation, the difference in an irradiation amount, the difference in an age in week, and the like, and it is difficult to distinguish the degree of physiological aging from the degree of damage caused by UV light in the wave number regions.

Comparative Example 2

Figure 10:
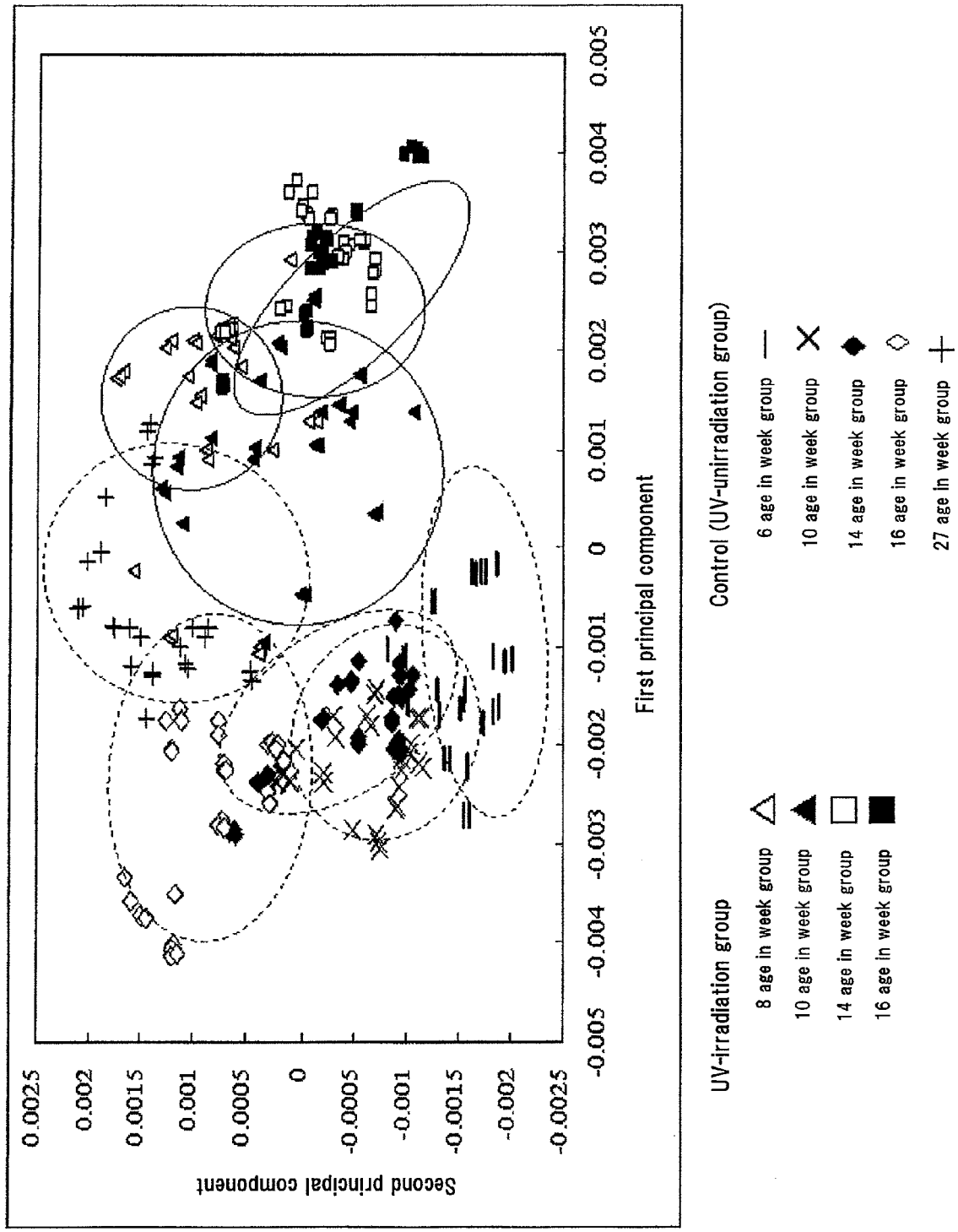
FIG. 10 is a diagram displaying a relationship between the degree of damage caused by UV light and the degree of physiological aging, which are results of a skin of a hairless mouse shown in Comparative Example 2, using a scatter diagram.
Figure 11:
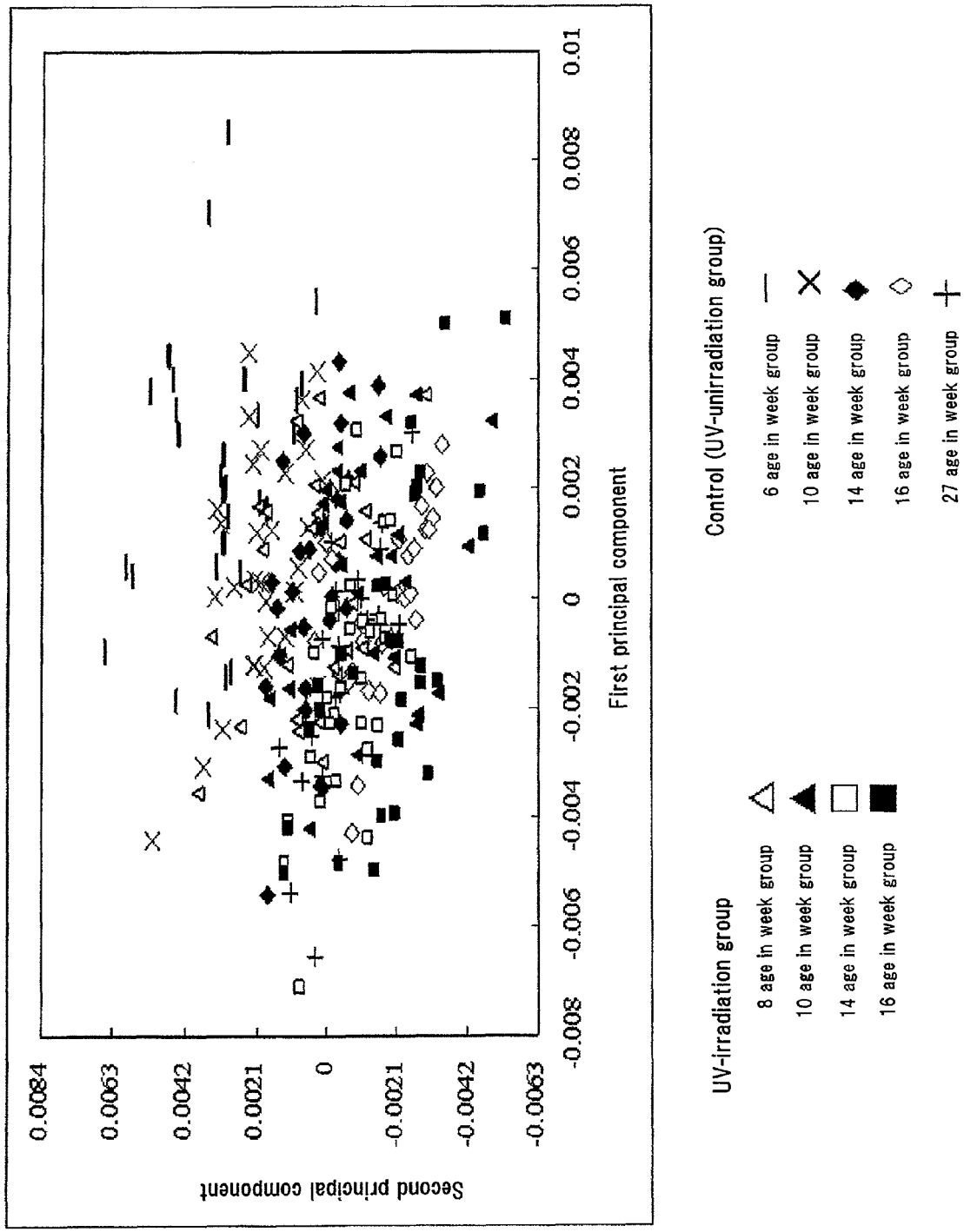
FIG. 11 is a diagram displaying a relationship between the degree of damage caused by UV light and the degree of physiological aging, which are results of the skin of a hairless mouse shown in Comparative Example 2, using a scatter diagram.

Scatter diagrams created from the results obtained by performing data processing and principal component analysis in wave number regions of 8000 to 6000 $cm^{-1}$ and 5490 to 5000 $cm^{-1}$ in Example 1 and are shown in FIG. 10 (wave number regions of 8000 to 6000 $cm^{-1}$ and 5490 to 5000 $cm^{-1}$) and FIG. 11 (wave number regions of 4480 to 4000 $cm^{-1}$). As shown in FIGS. 10 and 11, it is understood that the skins of hairless mice are not categorized depending upon the presence/absence of UV irradiation, the difference in an irradiation amount, the difference in an age in week, and the like, and it is difficult to distinguish the degree of physiological aging from the degree of damage caused by UV light in the wave number regions.

Comparative Example 3

Figure 12:
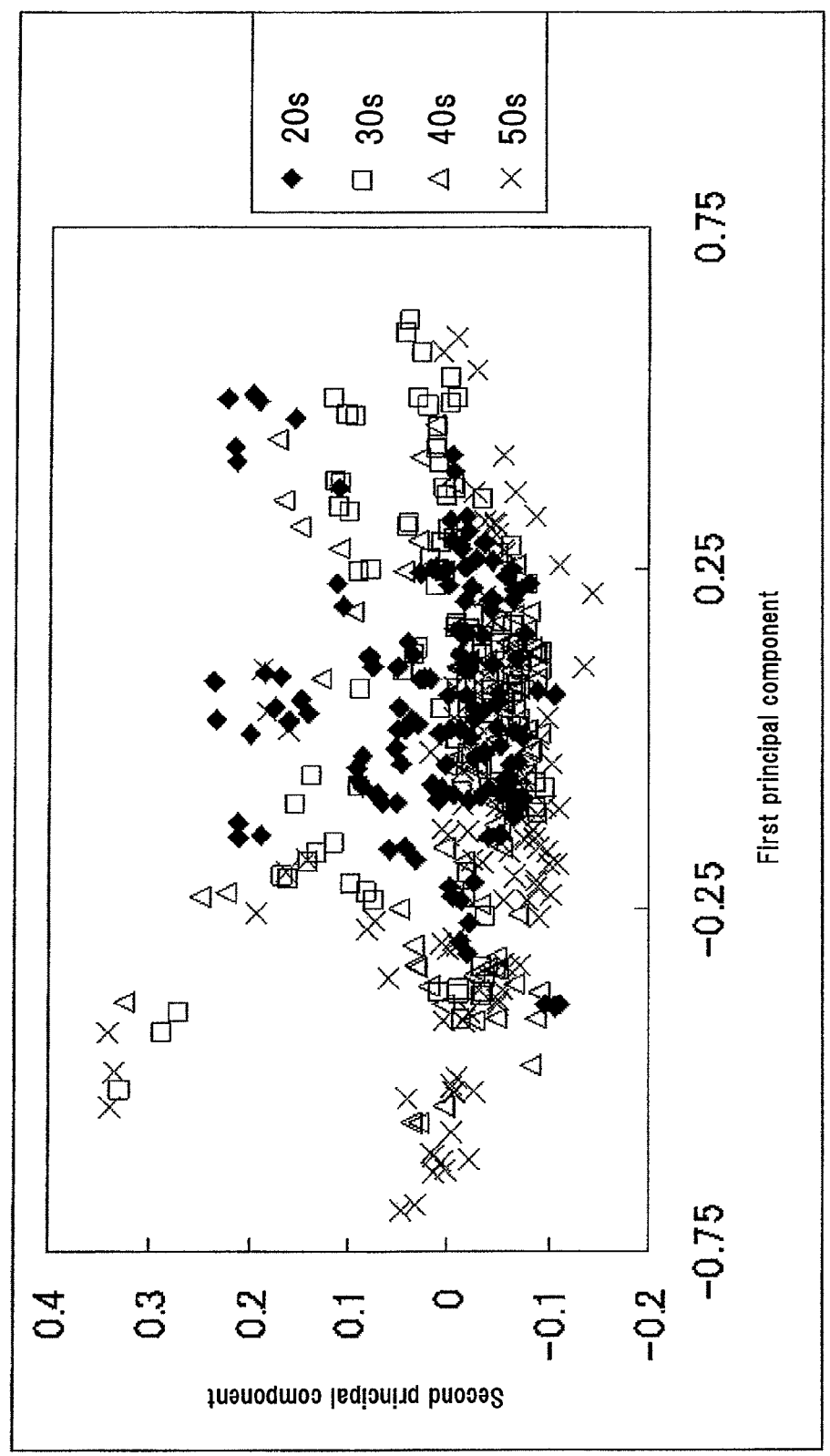
FIG. 12 is a diagram displaying a relationship between the degree of damage caused by UV light and the degree of physiological aging, which are results of a skin of a human being shown in Comparative Example 3, using a scatter diagram.

Scatter diagrams created from the results obtained by performing data processing and principal component analysis in wave number regions of 8000 to 4000 $cm^{-1}$ in Example 3 is shown in FIG. 12. As shown in FIG. 12, it is understood that the human skins are not categorized depending upon the generation and it is difficult to distinguish the degree of physiological aging from the degree of damage caused by UV light in the wave number regions.

Comparative Example 4

Figure 13:
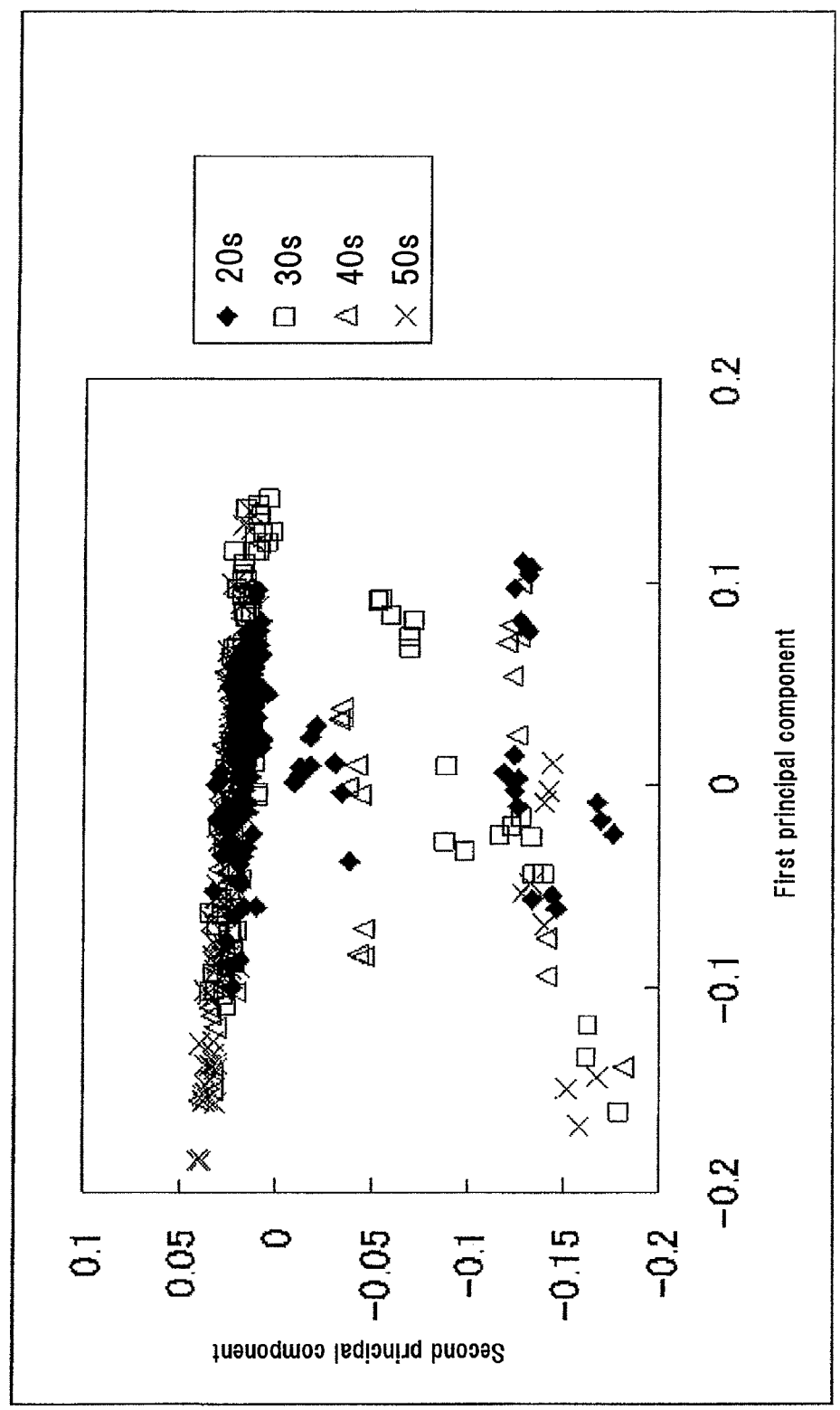
FIG. 13 is a diagram displaying a relationship between the degree of damage caused by UV light and the degree of physiological aging, which are results of a skin of a human being in Comparative Example 4, using a scatter diagram.
Figure 14:
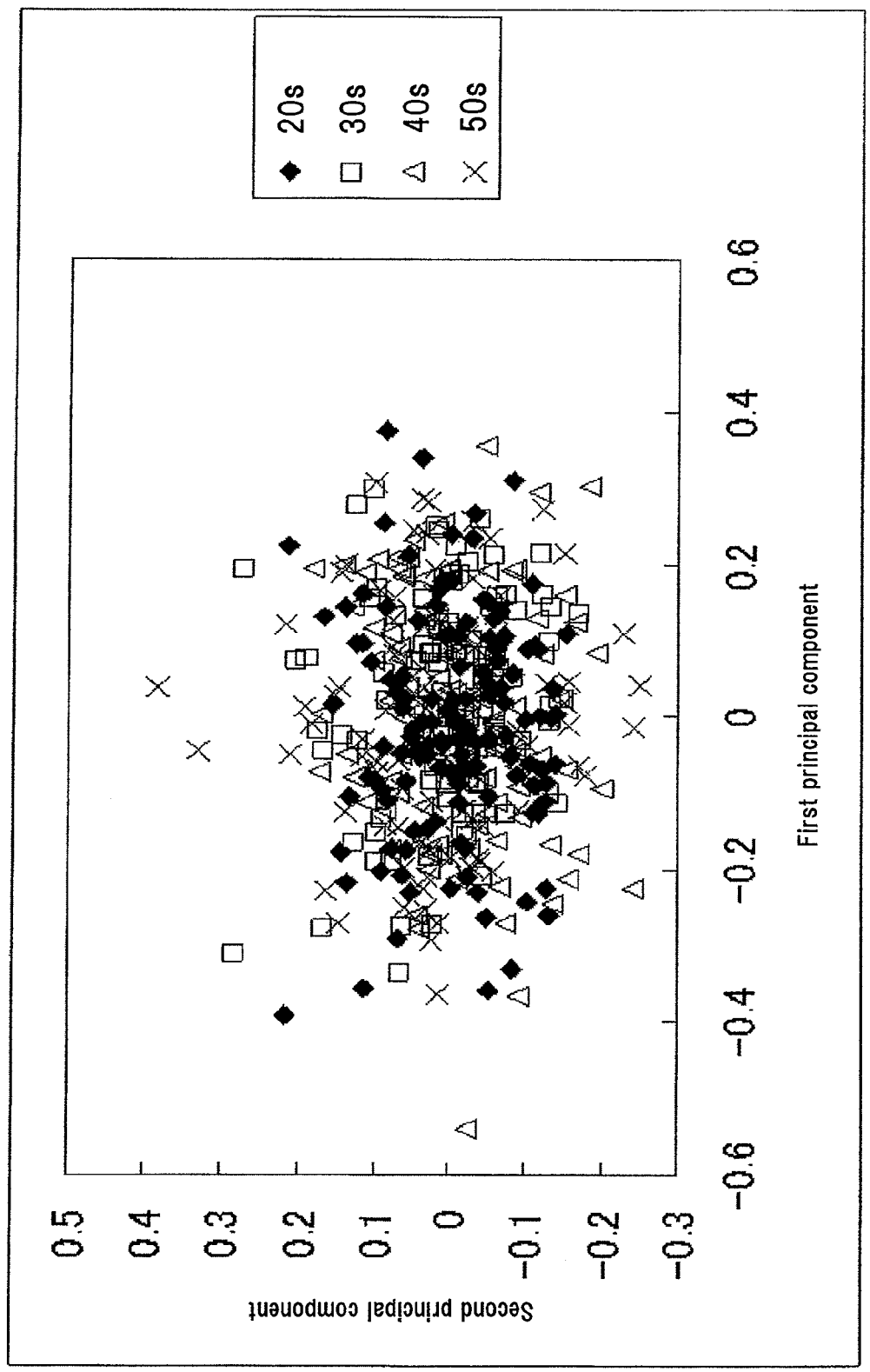
FIG. 14 is a diagram displaying a relationship between the degree of damage caused by UV light and the degree of physiological aging, which are results of the skin of a human being shown in Comparative Example 4, using a scatter diagram.
Figure 15:
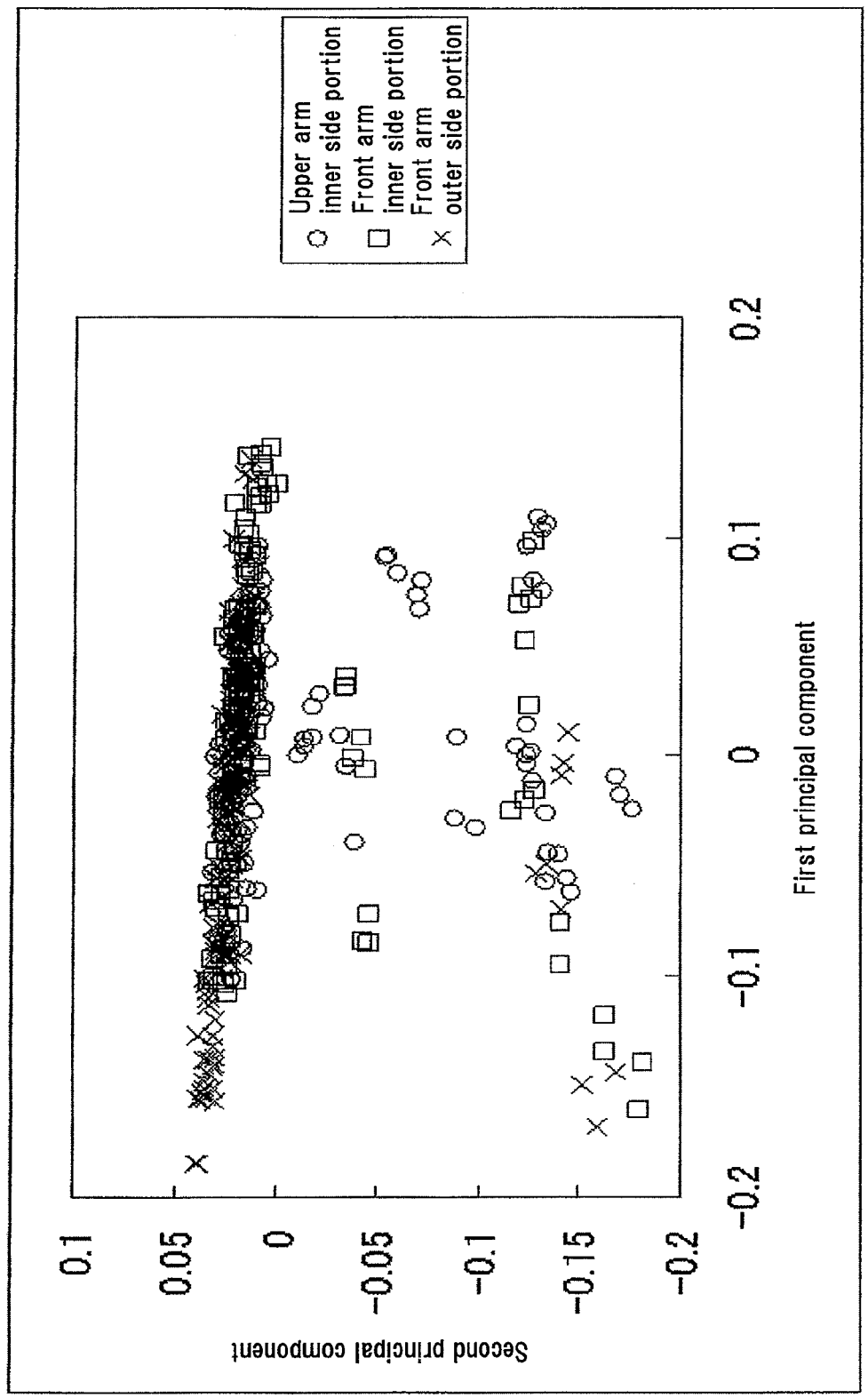
FIG. 15 is a diagram displaying a relationship between the degree of damage caused by UV light and the degree of physiological aging, which are results of the skin of a human being shown in Comparative Example 4, using a scatter diagram.
Figure 16:
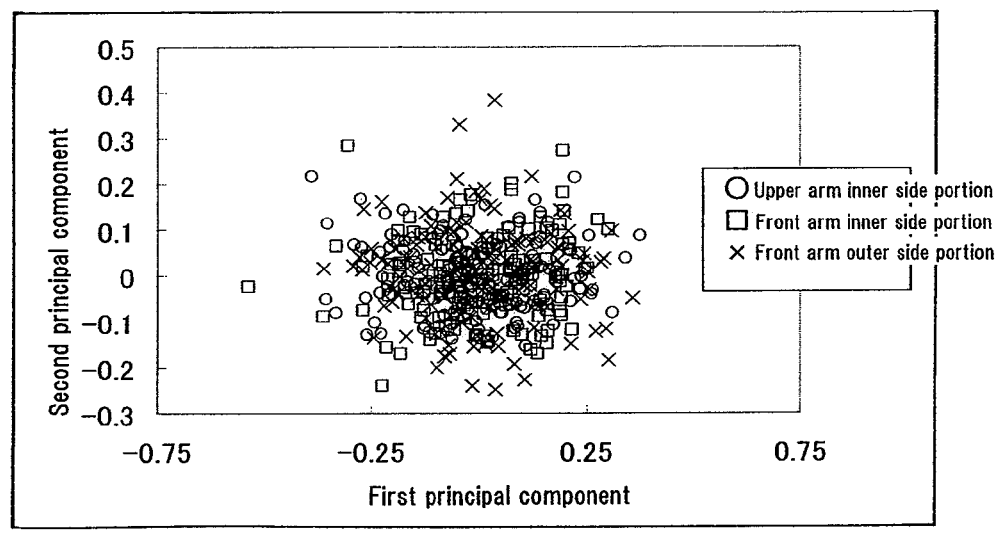
FIG. 16 is a diagram displaying a relationship between the degree of damage caused by UV light and the degree of physiological aging, which are results of the skin of a human being shown in Comparative Example 4, using a scatter diagram.

Scatter diagrams created from the results obtained by performing data processing and principal component analysis in wave number regions of 8000 to 6000 $cm^{-1}$ and 4480 to 4000 $cm^{-1}$ are shown in FIG. 13 (wave number regions of 8000 to 6000 $cm^{-1}$), FIG. 14 (wave number regions of 4480 to 4000 $cm^{-1}$), FIG. 15 (wave number regions of 8000 to 6000 $cm^{-1}$), and FIG. 16 (wave number regions of 4480 to 4000 $cm^{-1}$) in Example 3. As shown in FIGS. 13 to 16, it is understood that the human skins are not categorized depending upon the generation and site, and it is difficult to distinguish the degree of physiological aging from the degree of damage caused by UV light in the wave number regions.

Example 4

In the near infrared absorption spectrum of the skin sample collection obtained from the skins of the hairless mice, data processing was performed with respect to the wave number regions of 6850 to 6620 $cm^{-1}$, 6540 to 5990 $cm^{-1}$, 5240 to 5180 $cm^{-1}$, 5030 to 4980 $cm^{-1}$, 4760 to 4720 $cm^{-1}$, and 4650 to 4610 $cm^{-1}$ of an amide bond (CONH). Specifically, the mean center and standard normal variant (SNV) were performed, and thereafter, secondary differential was performed.

Figure 17:
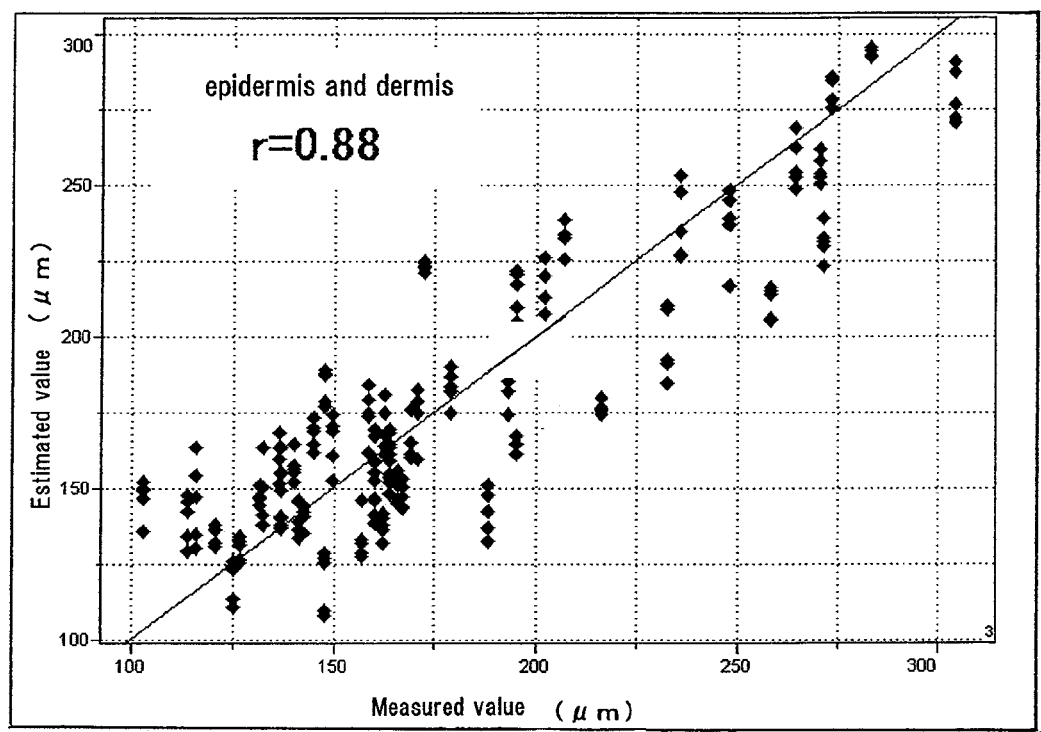
FIG. 17 is a diagram showing an estimated model (calibration line) of the thickness of a skin (an epidermis and a dermis) in a skin sample collection of a hairless mouse.
Figure 18:
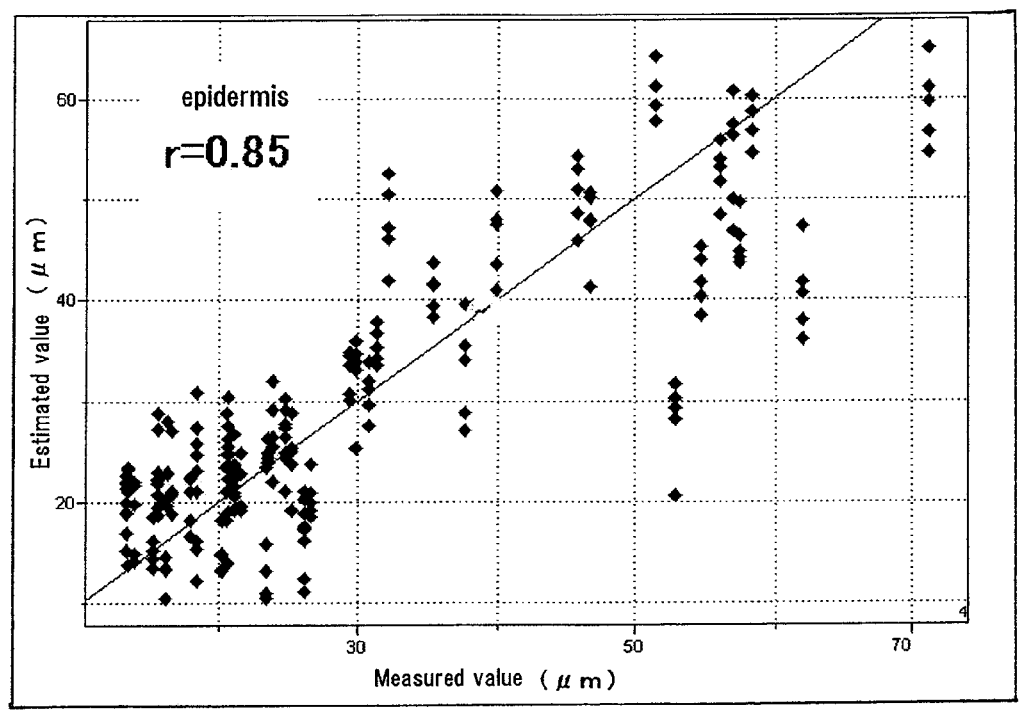
FIG. 18 is a diagram showing an estimated model (calibration line) of the thickness of an epidermis in the skin sample collection of a hairless mouse.
Figure 19:
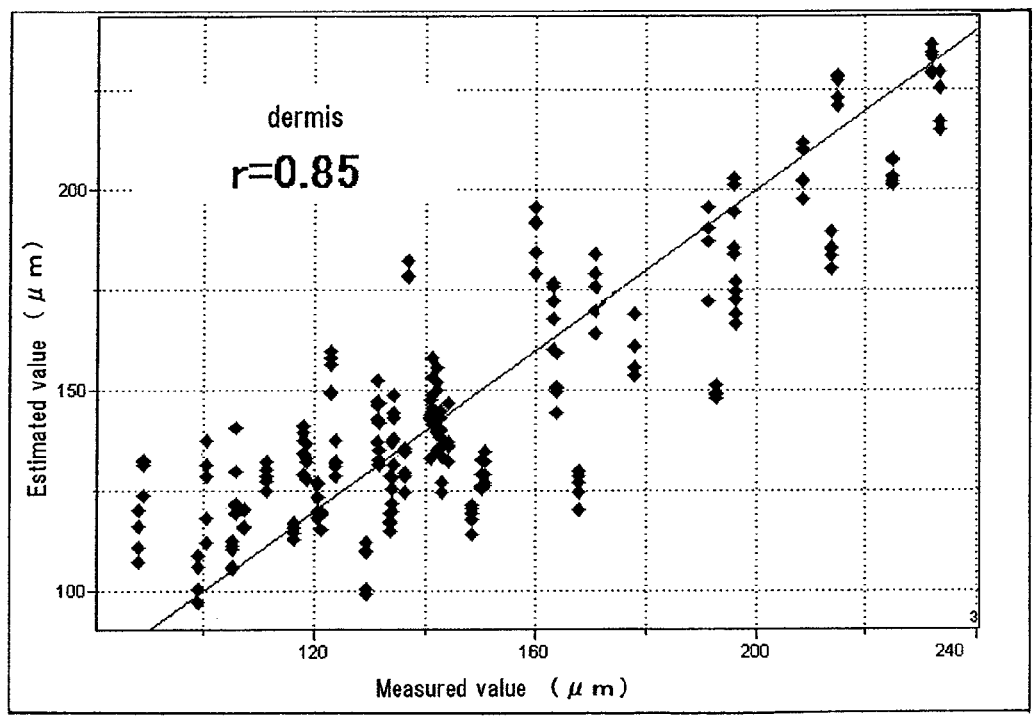
FIG. 19 is a diagram showing an estimated model (calibration line) of the thickness of a dermis in the skin sample collection of a hairless mouse.

The spectrum subjected to the data processing was divided for each 4 $cm^{-1}$, and a spectrum value (a secondary differential value of an absorbance) for each of the divided spectra was calculated. A matrix was created assuming the calculated spectrum value and thickness of a skin (at least one of an epidermis and a dermis) as a column and the contents of treatment (the presence/absence of UV irradiation, the difference in an irradiation amount, and the difference in an age in week) with respect to the skin as a row. The created matrix was subjected to regression analysis using the PLS. Estimation models (calibration lines, correlation coefficients) of each epidermal thickness and dermal thickness of a skin, which are the obtained analysis results, are shown in FIGS. 17 to 19. It is understood from FIGS. 17 to 19 that each epidermal thickness and dermal thickness of a skin can be estimated with high precision in the hairless mice. The data processing and the PLS were performed using the multivariate analysis software (Pirouette (registered trademark) Version 3.11; GL Sciences Inc.).

Example 5

Using FIGS. 17 to 19 obtained in Example 4, each thickness of a skin (epidermis and dermis), an epidermis, and a dermis of the hairless mice in the UV-irradiated 14-week-old group and the UV-unirradiated 14-week-old group were estimated (see Table 3). It is understood from Table 1 that each thickness was estimated with a high precision of about 10% of relative standard deviation.

TABLE 3

| Estimation of mouse skin thickness | UV-irradiated group average ± SD(μm) | UV-unirradiated group average ± SD(μm) |
|---|---|---|
| Epidermis | 58.9 ± 10.4 | 18.0 ± 5.8 |
| Dermis | 222.9 ± 27.7 | 131.4 ± 13.4 |
| Skin | 281.8 ± 34.8 | 149.3 ± 13.1 |

Example 6

Figure 20:
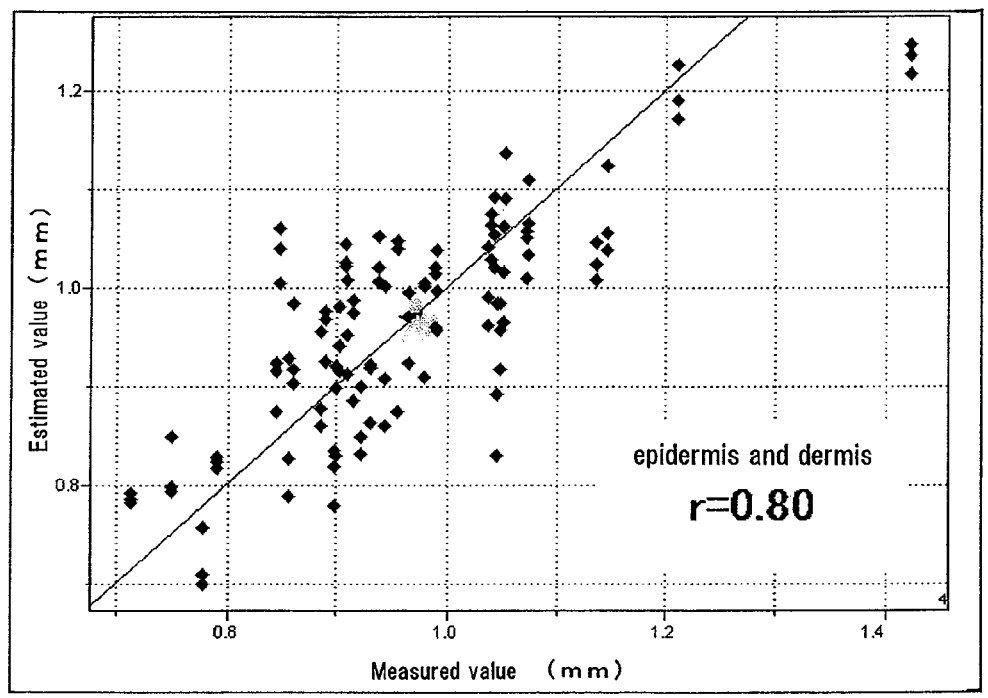
FIG. 20 is a diagram showing an estimated model (calibration line) of the thickness of a skin (an epidermis and a dermis) in a skin sample collection of a human being.
Figure 21:
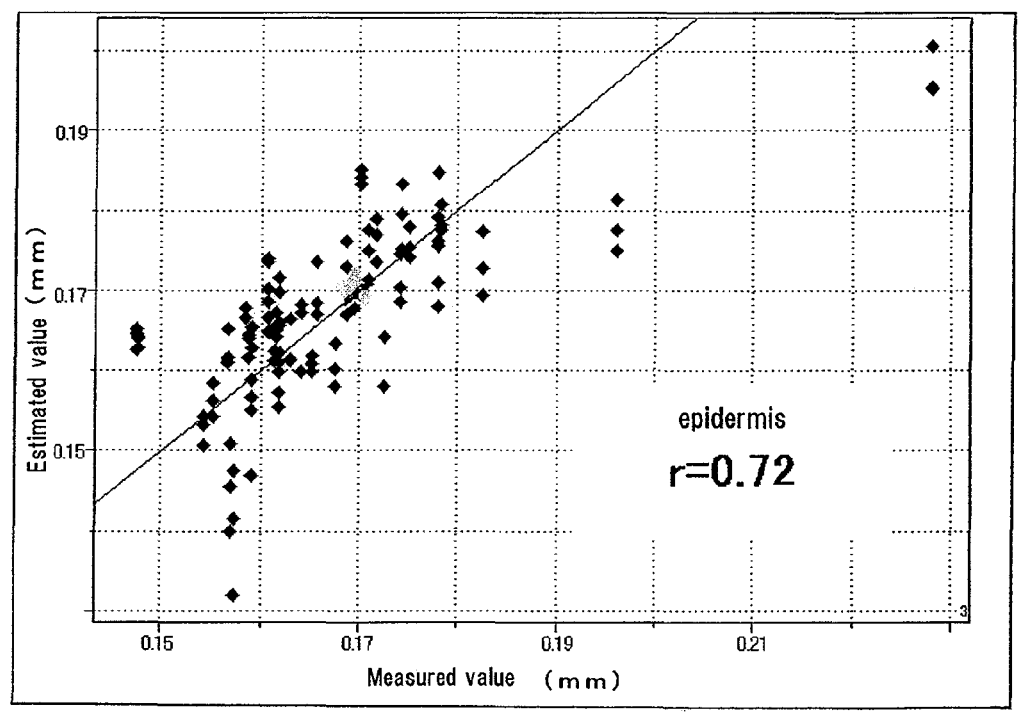
FIG. 21 is a diagram showing an estimated model (calibration line) of the thickness of an epidermis in the skin sample collection of a human being.
Figure 22:
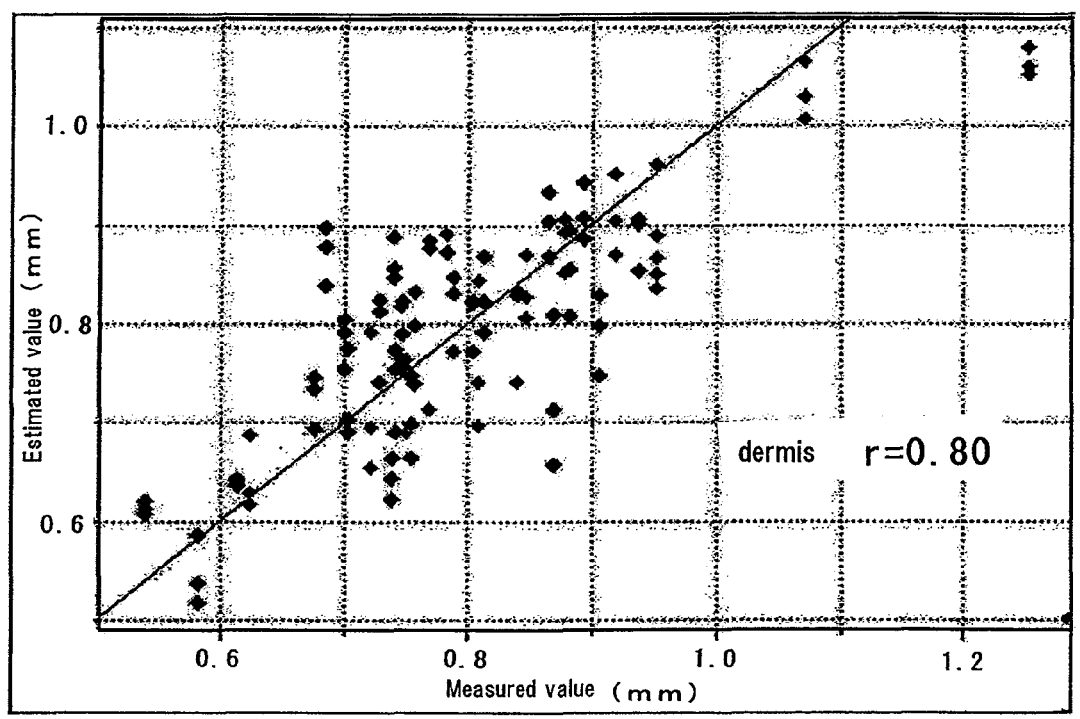
FIG. 22 is a diagram showing an estimated model (calibration line) of the thickness of a dermis in the skin sample collection of a human being.

The PLS regression analysis was performed in the same procedure by replacing the skin of the hairless mouse in Example 4 by the skin of a female subject shown in the human skin sample. The estimation models (calibration lines and correlation coefficients) of each epidermal thickness and dermal thickness of a skin, which are the obtained analysis results, are shown in FIGS. 20 to 22. It is understood from FIGS. 20 to 22 that each epidermal thickness and dermal thickness of a skin can be estimated with a high precision even in a human being.

Example 7

Using FIGS. 20 to 22 obtained in Example 6, each thickness of a skin (epidermis and dermis), an epidermis, and a dermis of an upper arm inner side portion of a female subject in forties (see Table 4). It is understood from Table 4 that relative standard deviations (coefficients of variation) can be estimated with a high precision of about 10%.

TABLE 4

| Estimation of human skin thickness | Female upper arm inner side portion Average ± SD(μm) |
|---|---|
| Epidermis | 157.6 ± 23.4 |
| Dermis | 743.7 ± 71.9 |
| Skin | 901.3 ± 80.7 |

Example 8

Each thickness of a skin (epidermis and dermis), an epidermis, and a dermis of an upper arm inner side portion of female subjects in forties was estimated using the estimation models (calibration lines) obtained by performing the PLS regression analysis in the same procedure while replacing the wave number regions of the near infrared absorption spectra in Examples 4 and 6 by 6940 to 6850 cm$^{-1}$, 6710 to 6540 cm$^{-1}$, 6250 to 6170 cm$^{-1}$, 5130 to 5080 cm$^{-1}$, 4950 to 4850 cm$^{-1}$, 4760 to 4690 cm$^{-1}$, and 4670 to 4610 cm$^{-1}$, which are structural characteristics of amide (CONH$_2$) (see Table 5). It is understood from Table 5 that relative standard deviations (coefficients of variation) can be estimated with a high precision of about 15%.

TABLE 5

| Estimation of human skin thickness | Female upper arm inner side portion Average ± SD(μm) |
|---|---|
| Epidermis | 157.6 ± 25.3 |
| Dermis | 743.7 ± 97.7 |
| Skin | 901.3 ± 98.2 |

Comparative Example 5

Each thickness of a skin (epidermis and dermis), an epidermis, and a dermis of an upper arm inner side portion of female subjects in forties was estimated using estimation models (calibration lines) obtained by performing the PLS regression analysis in the same procedure while replacing the wave number regions of the near infrared absorption spectra in Examples 4 and 6 by 8000 to 4000 cm$^{-1}$. It is understood that the relative standard deviations (coefficients of variation) are 20 to 30% or more, and each thickness cannot be estimated so effectively as in the invention of the present application in terms of the measurement of each thickness of a skin (epidermis and dermis), an epidermis, and a dermis.

Comparative Example 6

Figure 23:
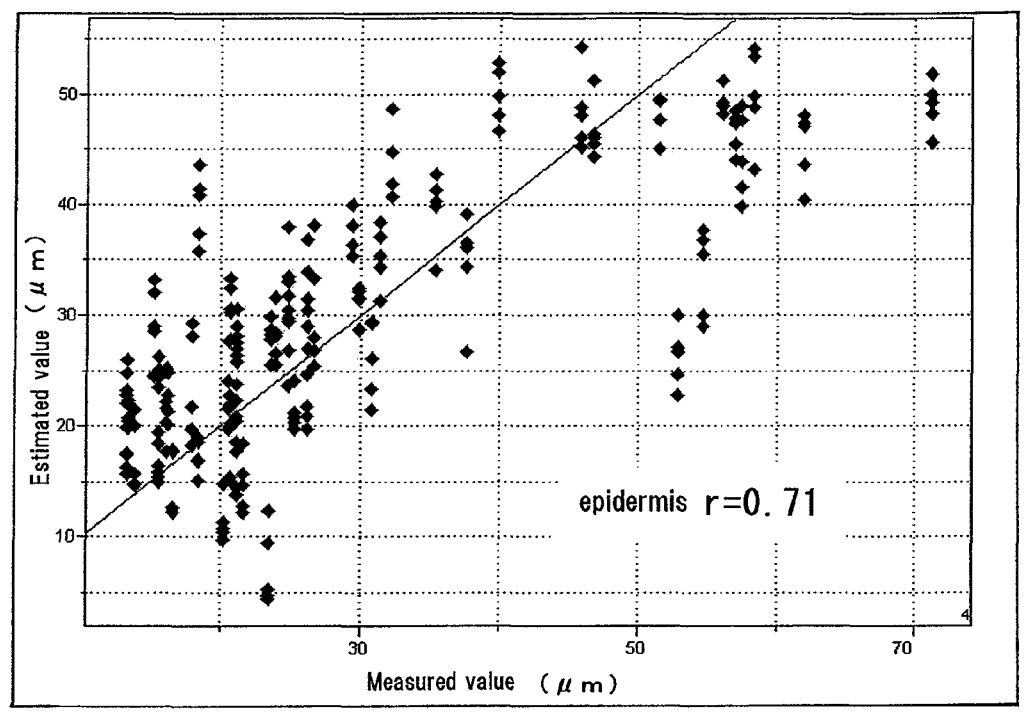
FIG. 23 is a diagram showing an estimated model (calibration line) of the thickness of an epidermis in the skin sample collection of a hairless mouse.
Figure 24:
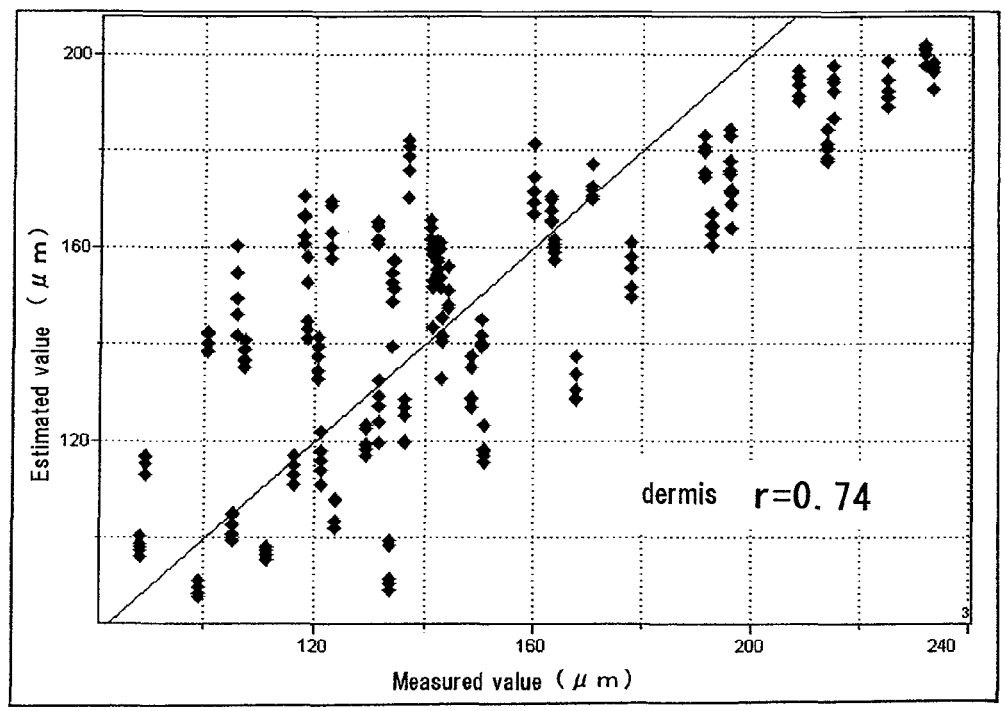
FIG. 24 is a diagram showing an estimated model (calibration line) of the thickness of a dermis in the skin sample collection of a hairless mouse.
Figure 25:
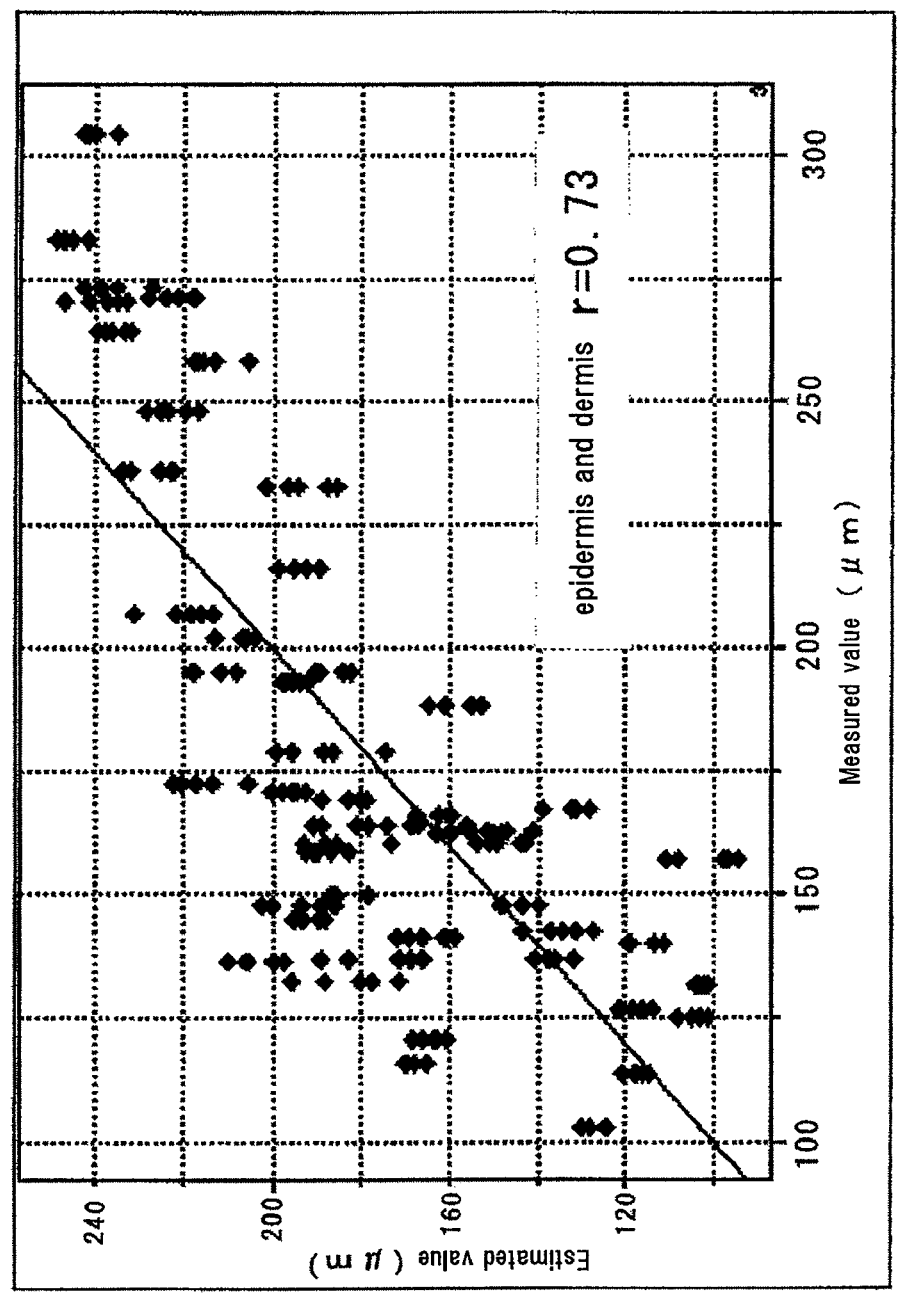
FIG. 25 is a diagram showing an estimated model (calibration line) of the thickness of a skin (an epidermis and a dermis) in the skin sample collection of a hairless mouse.

The PLS regression analysis was performed in the same procedure while replacing the wave number regions of an amide bond (CONH) in Example 4 by the wave number regions of 7380 to 7330 cm$^{-1}$, 5850 to 5780 cm$^{-1}$, 5650 to 5600 cm$^{-1}$, and 4400 to 4380 cm$^{-1}$ of a methyl bond (CH$_3$). The obtained estimation models (calibration lines) of each thickness of an epidermis, a dermis, and a skin (epidermis and dermis) are shown in FIGS. 23 to 25. It is understood from FIGS. 23 to 25 that the coefficients of correlation of the estimation models are 0.71 to 0.74, and each thickness of an epidermis, a dermis, and a skin (epidermis and dermis) cannot be estimated with a high precision as in the case of the wave number region of an amide bond (CONH) in the hairless mice. Using FIGS. 23 to 25, each thickness of a skin (epidermis and dermis), an epidermis, and a dermis of the hairless mice in the UV-irradiated 14-week-old group and the UV-unirradiated 14-week-old group was estimated (see Table 6). It is understood from Table 6 that the relative standard deviations (coefficients of variation) increase by around 20 to 30%, and each thickness of a skin (epidermis and dermis), an epidermis, and a dermis cannot be estimated so effectively as in the invention of the present application.

TABLE 6

| Estimation of mouse skin thickness | UV-irradiated group average ± SD(μm) | UV-unirradiated group average ± SD(μm) |
|---|---|---|
| Epidermis | 58.9 ± 12.7 | 18.0 ± 6.7 |
| Dermis | 222.9 ± 35.4 | 131.4 ± 21.8 |
| Skin | 281.8 ± 49.6 | 149.3 ± 30.9 |

Comparative Example 7

Figure 26:
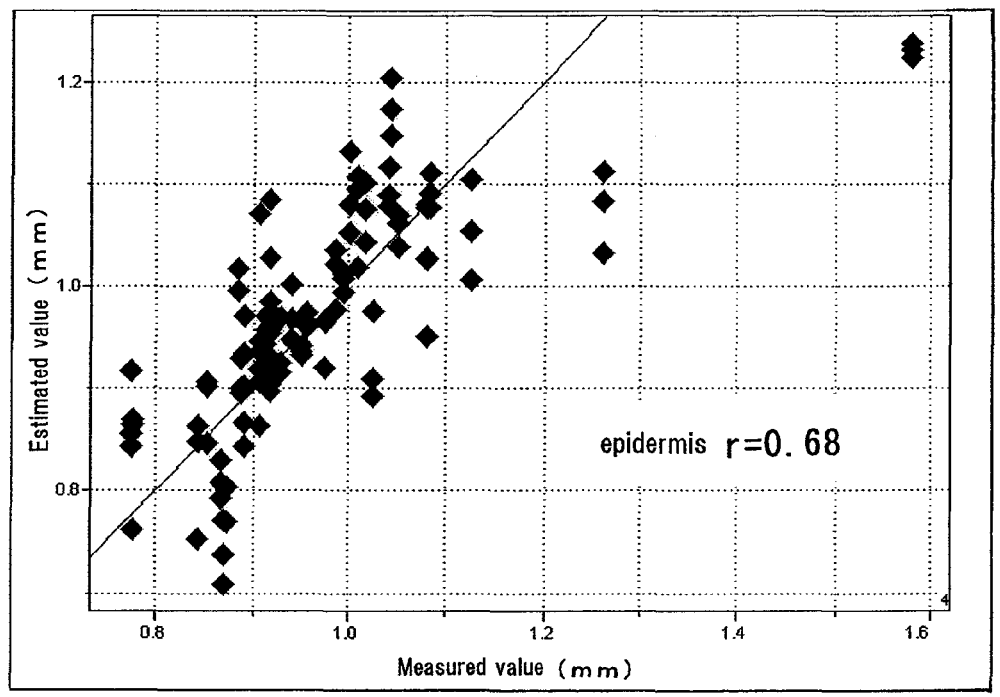
FIG. 26 is a diagram showing an estimated model (calibration line) of the thickness of an epidermis in the skin sample collection of a human being.
Figure 27:
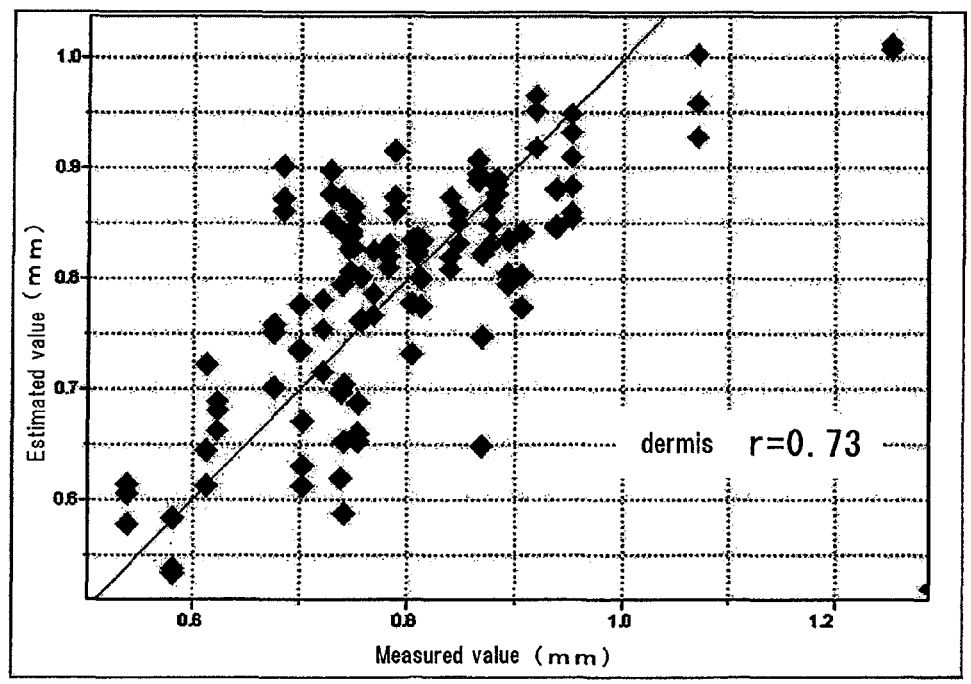
FIG. 27 is a diagram showing an estimated model (calibration line) of the thickness of a dermis in the skin sample collection of a human being.
Figure 28:
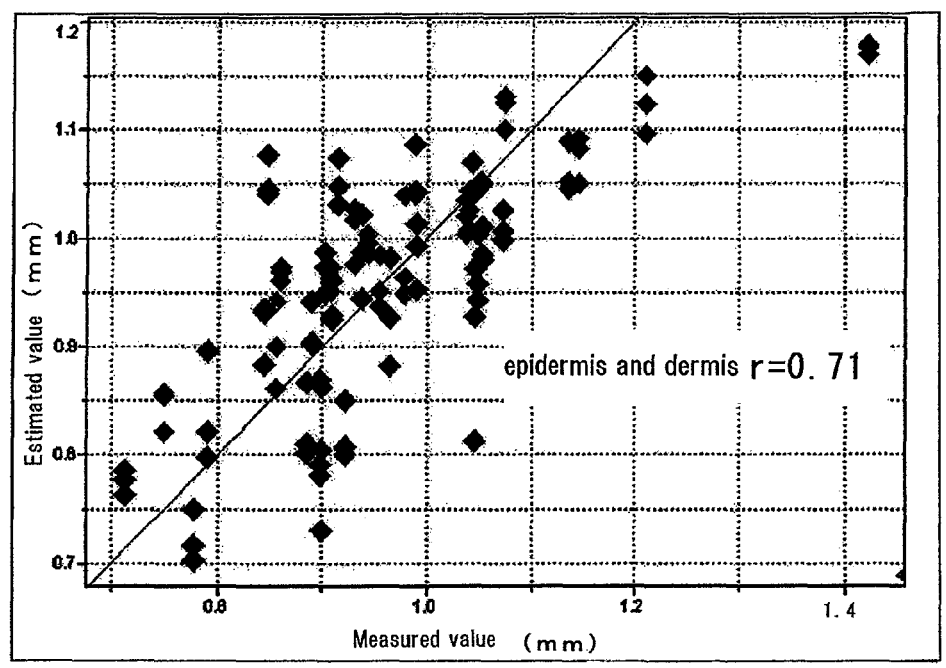
FIG. 28 is a diagram showing an estimated model (calibration line) of the thickness of a skin (an epidermis and a dermis) in the skin sample collection of a human being.

The PLS regression analysis was performed in the same procedure while replacing the wave number regions of an amide bond (CONH) in Example 6 by the wave number regions of 7380 to 7330 cm$^{-1}$, 5850 to 5780 cm$^{-1}$, 5650 to 5600 cm$^{-1}$, and 4400 to 4380 cm$^{-1}$ of a methyl bond (CH$_3$). The obtained estimation models (calibration lines) of each thickness of an epidermis, a dermis, and a skin (epidermis and dermis) are shown in FIGS. 26 to 28. It is understood from FIGS. 26 to 28 that the coefficients of correlation of the estimation models are 0.68 to 0.73, and each thickness of an epidermis, a dermis, and a skin (epidermis and dermis) cannot be estimated with a high precision as in the case of the wave number region of an amide bond (CONH) in the human being. Using FIGS. 26 to 28, each thickness of a skin (epidermis and dermis), an epidermis, and a dermis of an upper arm inner side portion of a female subject in forties was estimated (see Table 7). It is understood from Table 7 that the relative standard deviations (coefficients of variation) increase by around 20%, and each thickness of a skin (epidermis and dermis), an epidermis, and a dermis cannot be estimated so effectively as in the invention of the present application.

TABLE 7

| Estimation of human skin thickness | Female upper arm inner side portion average ± SD(μm) |
|---|---|
| Epidermis | 157.6 ± 25.9 |
| Dermis | 743.7 ± 151.5 |
| Skin | 901.3 ± 177.3 |

This application claims the benefit of Japanese Patent Application No. 2005-254324, filed Sep. 2, 2005, 2005-254326, filed Sep. 2, 2005, 2005-279292, filed Sep. 27, 2005, which are hereby incorporate by reference here in its entirely.

INDUSTRIAL APPLICABILITY

According to the present invention, at least one of the degree of damage of a skin of a human being and a mouse caused by UV light and the degree of physiological aging of a skin can be evaluated noninvasively and quantitatively. Further, according to the present invention, at least one of an epidermal thickness and a dermal thickness of a skin can be estimated noninvasively and quantitatively. By using the determination and estimation results, at least one of the degree of skin damage caused by UV light and the degree of physiological aging of a skin, and at least one of an epidermal thickness and dermal thickness of a skin can be monitored with time. Thus, in department stores, shops, or customers' houses, ordinary people can easily and adequately enjoy the evaluation of cosmetics with respect to the skin, the evaluation of skin conditions, and the advice and counseling regarding the selection of cosmetics and evaluation thereof.

What is claimed is:

1. A method of determining at least one of a degree of skin damage caused by UV light and a degree of physiological aging of skin from a near infrared absorption spectrum of the skin, comprising the steps of:
   (X1) correlating at least one of the degree of skin damage caused by UV light and the degree of physiological aging of the skin with the near infrared absorption spectrum of the skin, from analysis results of multivariate analysis of the near infrared absorption spectrum in a wave number region consisting of a measurement in wave number regions of 5990 to 5490 $cm^{-1}$ and 5000 to 4480 $cm^{-1}$ of two or more kinds of skin in which at least one of the degree of skin damage caused by UV light and the degree of physiological aging of the skin is known;
   (X2) obtaining a near infrared absorption spectrum in the wave number region of the skin in which at least one of the degree of skin damage caused by UV light and the degree of physiological aging of the skin to be evaluated is unknown; and
   (X3) determining at least one of the degree of skin damage caused by UV light and the degree of physiological aging of the skin from the near infrared absorption spectrum in the wave number region obtained in Step (X2) based on the correlation obtained in Step (X1).

2. A method according to claim 1, wherein both the degree of skin damage caused by UV light and the degree of physiological aging of the skin are determined simultaneously.

3. A method according to claim 1, wherein the multivariate analysis is a principal component analysis (PCA) method, SIMCA method or a KNN method.

4. A method of estimating at least one of an epidermal thickness and a dermal thickness of skin from a near infrared absorption spectrum of the skin, comprising the steps of:
   (Y1) correlating at least one of an epidermal thickness and a dermal thickness of the skin with the near infrared absorption spectrum in a wave number region of the skin, from analysis results of multivariate analysis of the near infrared absorption spectrum in measurement wave number regions selected from the group consisting of:
      (i) 6850 to 6620 $cm^{-1}$, 6540 to 5990 $cm^{-1}$, 5240 to 5180 $cm^{-1}$, 5030 to 4980 $cm^{-1}$, 4760 to 4720 $cm^{-1}$, and 4650 to 4610 $cm^{-1}$, and
      (ii) 6940 to 6850 $cm^{-1}$, 6710 to 6540 $cm^{-1}$, 6250 to 6170 $cm^{-1}$, 5130 to 5080 $cm^{-1}$, 4950 to 4850 $cm^{-1}$, 4760 to 4690 $cm^{-1}$, and 4670 to 4610 $cm^{-1}$,
   of two or more kinds of skin in which at least one of an epidermal thickness and a dermal thickness of the skin is known;
   (Y2) obtaining a near infrared absorption spectrum in the wave number region of the skin in which at least one of an epidermal thickness and a dermal thickness of the skin to be estimated is unknown; and
   (Y3) estimating at least one of the epidermal thickness and the dermal thickness of the skin from the near infrared absorption spectrum in the wave number region obtained in Step (Y2) based on the correlation obtained in Step (Y1).

5. A method according to claim 4, wherein both the epidermal thickness and the dermal thickness of the skin are estimated simultaneously.

6. A method according to claim 4, wherein the multivariate analysis is a partial least squares (PLS) method or a principal component regression (PCR) analysis method.

7. A method of selecting a cosmetic, comprising the step of selecting a cosmetic using the method according to claim 1 or 4.

8. A method of monitoring a skin condition, comprising the step of capturing a change of the skin with time chronologically using the method according to claim 1 or 4.

9. A method of monitoring according to claim 8, comprising the step of confirming effects of treatment with respect to the skin.

10. A method of evaluating a cosmetic, comprising the step of comparing a state or a thickness of the skin before and after administration of the cosmetic and evaluating the cosmetic with the change as an index, using the method according to claim 1 or 4.

11. A method of evaluating a cosmetic according to claim 10, comprising the step of evaluating that a cosmetic has a wrinkle disappearing function in a case where a dermal thickness of the skin increases due to the administration of the cosmetic.

* * * * *

UNITED STATES PATENT AND TRADEMARK OFFICE
CERTIFICATE OF CORRECTION

PATENT NO. : 7,820,972 B2  
APPLICATION NO. : 12/064001  
DATED : October 26, 2010  
INVENTOR(S) : Miyamae et al.

Page 1 of 1

It is certified that error appears in the above-identified patent and that said Letters Patent is hereby corrected as shown below:

Column 3, Line 14, "of skindamage caused" should be changed to --of skin damage caused--

Column 4, Line 1, "6710 to 6540 m$^{-1}$," should be changed to --6710 to 6540 cm$^{-1}$,--

Column 6, Line 66, "elastin, skinthickness," should be changed to --elastin, skin thickness,--

Column 11, Line 24, "6710 to 6540 m$^{-1}$," should be changed to --6710 to 6540 cm$^{-1}$,--

Column 11, Line 56, "deta processing of" should be changed to --data processing of--

Column 11, Line 58, "6710 to 6540 m$^{-1}$," should be changed to --6710 to 6540 cm$^{-1}$,--

Column 24, Line 19, "4760 to 4720 m$^{-1}$,and" should be changed to --4760 to 4720 cm$^{-1}$, and--

Signed and Sealed this  
Twenty-fourth Day of May, 2011

David J. Kappos  
*Director of the United States Patent and Trademark Office*